United States Patent
Lin et al.

(10) Patent No.: US 8,318,167 B2
(45) Date of Patent: Nov. 27, 2012

(54) METHODS AND COMPOSITIONS FOR REGULATING IRON HOMEOSTASIS BY MODULATION OF BMP-6

(75) Inventors: Herb Lin, Watertown, MA (US); Jodie Babitt, Newton Highlands, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 12/618,319

(22) Filed: Nov. 13, 2009

(65) Prior Publication Data
US 2010/0136015 A1 Jun. 3, 2010

Related U.S. Application Data

(60) Provisional application No. 61/114,290, filed on Nov. 13, 2008, provisional application No. 61/141,155, filed on Dec. 29, 2008.

(51) Int. Cl.
*A61K 39/395* (2006.01)
*A61K 39/00* (2006.01)
*C07K 16/22* (2006.01)

(52) U.S. Cl. ............... 424/141.1; 424/139.1; 424/145.1; 530/388.1; 530/388.24

(58) Field of Classification Search ........................ None
See application file for complete search history.

(56) References Cited

U.S. PATENT DOCUMENTS

| | | | |
|---|---|---|---|
| 2003/0224501 A1* | 12/2003 | Young et al. ................ | 435/226 |
| 2004/0014141 A1 | 1/2004 | Woolf et al. | |
| 2006/0063208 A1 | 3/2006 | Woolf et al. | |
| 2006/0239951 A1 | 10/2006 | Valentin et al. | |
| 2007/0124825 A1 | 5/2007 | Nicolas et al. | |
| 2008/0260736 A1 | 10/2008 | Lin et al. | |

FOREIGN PATENT DOCUMENTS

| | | |
|---|---|---|
| WO | 02/098444 A2 | 12/2002 |
| WO | 03/089608 A2 | 10/2003 |
| WO | 2004/003150 A2 | 1/2004 |
| WO | 2004/004750 A2 | 1/2004 |
| WO | 2004/016606 A2 | 2/2004 |
| WO | 2005/028517 A2 | 3/2005 |
| WO | WO-2008124768 A1 | 10/2008 |

OTHER PUBLICATIONS

Kautz et al., Blood, 2008, vol. 112:1503-1509.*
Weinstein et al., "Inappropriate expression of Hepcidin is associated with iron refractory anemia: implications for the anemia of chronic disease", Blood (2002), 100(10): 3776-3781.
Nemeth et al., "Hepcidin is decreased in TRF2 hemochromatosis", Blood (2005), 105(4): 1803-1806.
Database WPI Week 2001 Thomson Scientific (2001), AN 2001-317422 & CN 1284380A, INST Hematology Chinese Acad Medical Sci.
Roetto et al., "Mutant antimicrobial peptide Hepcidin is associated with severe juvenile hemochromatosis", Nature Genetics (2003), 33(1):21-22.
Krijt et al., "Expression of Rgmc, the murine ortholog of hemojuvelin gene, is modulated by development and inflammation, but not by iron status or Erythropoietin", Blood (2004), 104(13).
European Examination Report, Application No. EP 06735151.0, Mail Date: Apr. 16, 2010.
Andriopoulos, B. Jr., et al., (2009), "BMP6 is a key endogenous regulator of hepcidin expression and iron metabolism," Nat. Genet., 41(4):482-487.
Babitt, J.L. et al., (2007), "Modulation of bone morphogenetic protein signaling in vivo regulates systemic iron balance," J. Clin. Invest., 117(7):1933-1939.
Dai J. et al., (2005), "Bone morphogenetic protein-6 promotes osteoblastic prostate cancer bone metastases through a dual mechanism," Cancer Res., 65(18):8274-8285.
Xia Y. et al., (2008), "Hemojuvelin regulates hepcidin expression via a selective subset of BMP ligands and receptors independently of neogenin," Blood, 111(10):5195-5204.
Andrews (2008), "Forging a field: the golden age of iron biology," Blood 112:219-30.
Babitt et al. (2005), "Repulsive guidance molecule (RGMa), a DRAGON homologue, is a bone morphogenetic protein co-receptor," J. Biol. Chem. 280:29820-29827.
Babitt et al. (2006), "Bone morphogenetic protein signaling by hemojuvelin regulates hepcidin expression," Nat. Genet. 38:531-539.
Balemans et al. (2002), "Extracellular regulation of BMP signaling in vertebrates: a cocktail of modulators," Dev Biol. 250:231-250.
Huang et al. (2005), "A mouse model of juvenile hemochromatosis," J. Clin. Invest., 115:2187-2191.
Kautz et al., (2008), "Iron regulates phosphorylation of Smad1/5/8 and gene expression of Bmp6, Smad7, Id1, and Atoh8 in the mouse liver," Blood, 112: 1503-9.
Knutson et al. (2005), "Iron release from macrophages after erythrophagocytosis is up-regulated by ferroportin 1 overexpression and down-regulated by hepcidin," Proc Natl Acad Sci USA 102:1324-8.
Nemeth et al. (2004), "Hepcidin regulates cellular iron efflux by binding to ferroportin and inducing its internalization. Science," Science 306:2090-2093.
Nemeth et al. (2004), "IL-6 mediates hypoferremia of inflammation by inducing the synthesis of the iron regulatory hormone hepcidin," J. Clin. Invest. 113:1271-1276.
Nicolas et al. (2002), "The gene encoding the iron regulatory peptide hepcidin is regulated by anemia, hypoxia, and inflammation," J. Clin. Invest. 110:1037-1044.
Niederkofler et al. (2005), "Hemojuvelin is essential for dietary iron sensing, and its mutation leads to severe iron overload," J Clin. Invest., 115:2180-6.
Papanikolaou et al. (2004), "Mutations in HFE2 cause iron overload in chromosome 1q-linked juvenile hemochromatosis," Nat. Genet. 36:77-82.

(Continued)

Primary Examiner — Xiaozhen Xie
(74) Attorney, Agent, or Firm — Lathrop & Gage LLP; Sean M. Coughlin, Esq.

(57) ABSTRACT

Modulation of iron homeostasis by regulating BMP-6 activity is provided. Methods of using BMP-6 and BMP-6 protein-specific reagents, such as antibodies, for altering serum iron levels in humans are provided. Such antibodies are useful in pharmaceutical compositions for the prevention and treatment of hemochromatosis and anemia of inflammation.

12 Claims, 14 Drawing Sheets

OTHER PUBLICATIONS

Pietrangelo (2006), "Hereditary hemochromatosis," Biochim. Biophys. Acta 1763:700-710.

Pigeon et al. (2001), "A new mouse liver-specific gene, encoding a protein homologous to human antimicrobial peptide hepcidin, is overexpressed during iron overload," J. Biol. Chem. 276:7811-7819.

Samad et al. (2004), "DRAGON: A Member of the Repulsive Guidance Molecule-Related Family of Neuronal- and Muscle-Expressed Membrane Proteins Is Regulated by DRG11 and Has Neuronal Adhesive Properties," J. Neurosci. 24: 2027-2036.

Samad et al. (2005), "DRAGON, a bone morphogenetic protein co-receptor," J. Biol. Chem. 280:14122-14129.

Shi et al. (2003), "Mechanisms of TGF-beta signaling from cell membrane to the nucleus," Cell. 113:685-700.

Simic et al. (2006), "Systemically administered recombinant BMP-6 restores bone in aged OVX rats by increasing bone formation and suppressing bone resorption," J. Biol. Chem. 281:25509-21.

Solloway et al. (1998), "Mice lacking Bmp6 function," Dev Genet. 22:321-39.

Truska et al. (2006), "Bone morphogenetic proteins 2, 4, and 9 stimulate murine hepcidin 1 expression independently of Hfe, transferrin receptor 2 (Tfr2), and IL-6," Proc. Natl. Acad. Sci. USA 103:10289-10293.

Verga Falzacappa et al. (2008), "A bone morphogenetic protein (BMP)-responsive element in the hepcidin promoter controls HFE2-mediated hepatic hepcidin expression and its response to IL-6 in cultured cells," J. Mol. Med. 86:531-40.

Wang et al. (2005), "A role of SMAD4 in iron metabolism through the positive regulation of hepcidin expression," Cell Metab. 2:399-409.

Xia et al. (2007), "Repulsive guidance molecule RGMa alters utilization of bone morphogenetic protein (BMP) type II receptors by BMP2 and BMP4," J. Biol. Chem. 282:18129-40.

Yu et al. (2008), "Dorsomorphin inhibits BMP signals required for embryogenesis and iron metabolism," Nat Chem. Biol. 4:33-41.

Weiss, Guenter, et al. "Anemia of Chronic Disease", The New England Journal of Medicine, 352;10, pp. 1011-1023, Mar. 10, 2005.

Third-Party Observation Concerning Patentability, EP Application No. 09826827.9, European Patent Office, dated Sep. 11, 2012.

* cited by examiner

METHODS AND COMPOSITIONS FOR REGULATING IRON HOMEOSTASIS BY MODULATION OF BMP-6

RELATED APPLICATIONS

This application claims priority from U.S. Provisional Patent Applications 61/114,290, filed on Nov. 13, 2008; and 61/141,155, filed on Dec. 29, 2008, incorporated by reference, herein, in their entireties.

GOVERNMENT INTERESTS

This invention was made with Government support under Grant Nos. DK071837, DK075846 awarded by the Public Health Services/National Institutes of Health. The Government has certain rights to this invention.

TECHNICAL FIELD OF THE INVENTION

The present invention relates generally to therapy, prevention and amelioration of iron homeostasis disorders. The invention is more specifically related to methods of using BMP-6 and BMP-6 protein-specific reagents, such as antibodies for altering serum iron, serum hemoglobin and/or hematocrit levels in humans. Such antibodies are useful in pharmaceutical compositions for the prevention and treatment of hemochromatosis and anemia of inflammation.

BACKGROUND OF THE INVENTION

Iron is an essential element required for growth and survival of almost every organism. Red blood cells (RBC) contain hemoglobin (Hb), a red, iron-rich protein that carries oxygen from the lungs to all of the body's muscles and organs where it reacts to provide the energy the body needs for its normal activities. When the number of red blood cells or the amount of hemoglobin they contain fall below normal, the body receives less oxygen and generates less energy than it needs to function properly. This condition in general is referred to as anemia. A common cause for anemia among infants and children is an iron deficiency. As many as 20% of children in the United States and 80% of children in developing countries will become anemic at some point by the age of 18 years. Martin, P. L., et al. The Anemias, Principles and Practices of Pediatrics, 1657 (2d ed., Lippincott 1994).

In mammals, the iron balance is primarily regulated at the level of duodenal absorption of dietary iron. In humans, hereditary hemochromatosis (HH) is a common autosomal recessive genetic disease caused by hyperabsorption of dietary iron leading to an iron overload in plasma and multiple organs, including in particular the pancreas, liver, and skin, and resulting in damages in these organs and tissues due to the iron deposits.

Juvenile hemochromatosis is an iron overload disorder caused by mutations in the gene encoding the major iron regulatory hormone hepcidin (HAMP) and hemojuvelin (HFE2). (Roetto, A., et al. 2003. *Nut. Genet.* 33:21-22; Papanikolaou, G., et al. 2004. *Nut. Genet.* 36:77-82.) It has been shown that hemojuvelin is a bone morphogenetic protein (BMP) co-receptor and that hemojuvelin-mediated BMP signals regulate hepcidin expression and iron metabolism. (Babitt, J. L., et al. 2006. *Nat. Genet.* 38:531-539; Babitt, J. L., et al. 2007. *J Clin Invest.* 117:1933-1939.) However, the endogenous BMP regulator(s) of hepcidin in vivo is unknown.

BMPs are members of the TGF-β superfamily, which is comprised of over 40 ligands. (Shi, Y., and Massague, J. 2003. *Cell.* 113:685-700.) These growth factors mediate diverse biological processes including cell proliferation, differentiation, apoptosis, and patterning. BMP/TGF-β superfamily ligands initiate an intracellular signaling cascade by binding to a complex of type I and type II serine threonine kinase receptors. The activated receptor complex phosphorylates intracellular Smad proteins, which then translocate to the nucleus to modulate gene expression.

Recently, a role for the BMP signaling pathway in regulating the major iron regulatory hormone hepcidin has been discovered. (Babitt, J. L., et al. 2006. *Nat. Genet.* 38:531-539; Babitt, J. L., H et al. *J Clin Invest.* 117:1933-1939; Wang, R. H., et al. 2005. *Cell Metab.* 2:399-409.) Secreted by the liver, hepcidin inhibits intestinal iron absorption and macrophage iron release by decreasing cell surface expression of the iron exporter ferroportin. (Nemeth, E., et al. 2004. *Science.* 306: 2090-2093). Hepcidin is upregulated by iron administration (Pigeon, C., et al. 2001. *J. Biol. Chem.* 276:7811-7819, Nicolas, G., et al. 2002. *J. Clin. Invest.* 110:1037-1044; Nemeth, E., et al. 2004. *J. Clin. Invest.* 113: 1271-1276.) and inhibited by anemia. (Nicolas, G., et al. 2002. *J. Clin. Invest.* 110:1037-1044) Hepcidin deficiency and unchecked ferroportin activity are the common pathogenic mechanisms underlying the genetic iron overload disorder hereditary hemochromatosis due to mutations in HAMP itself, HFE2, HFE, TFR2 (encoding transferrin receptor type 2), and rare mutations of SCLAOA1 (encoding ferroportin). (Pietrangelo, A. 2006. *Biochim Biophys Acta* 1763:700-710) Hepcidin is also upregulated by inflammatory cytokines, such as IL-6, and hepcidin excess is implicated in the pathogenesis of anemia of inflammation (Pigeon, C., et al. 2001. *J. Biol. Chem.* 276: 7811-7819, Nicolas, G., et al. 2002. *J. Clin. Invest.* 110:1037-1044; Nemeth, E., et al. 2004. *J. Clin. Invest.* 113: 1271-1276; Nemeth, E., et al. 2003. *Blood.* 101:246 1-2463; Weiss, G. and Goodnough, L. T. 2005. *N. Engl. J. Med.* 352:1011-1023; Andrews N C. 2008. *Blood.* 1122 19-30.)

Reduction of hepatic BMP signaling by a liver-specific conditional knockout of the common BMP/TGF-β intracellular mediator Smad4 (Wang, R. H., et al. 2005. *Cell Metab.* 2:399-409.), or by mutations in HFE2 (Papanikolaou, G., et al. 2004. *Nut. Genet.* 36:77-82; Babitt, J. L., et al. 2006. *Nat. Genet.* 38:531-539; Huang, F. W., et al. *J. Clin. Invest.* 115: 2187-2191; Niederkofler, V., Salie, R., Arber, S. 2005. *J Clin Invest.* 115:2180-6), which encodes the BMP co-receptor hemojuvelin, are associated with inappropriately low hepcidin expression and iron overload. BMP signals positively increase hepcidin expression at the transcriptional level in vitro. (Babitt, J. L., et al. 2006. *Nat. Genet.* 38:531-539; Babitt, J. L., H et al. *J Clin Invest.* 117:1933-1939; Wang, R. H., et al. 2005. *Cell Metab.* 2:399-409; Truksa, J., et al. 2006. *Proc. Natl. Acad. Sci. USA.* 103:10289-10293; Verga Falzacappa, M. V., et al. 2008. *J Mol. Med.* 86:531-40.). Iron administration in vivo increases hepatic BMP signaling (Yu, P. B., et al. 2008. *Nut Chem. Biol.* 4:33-41). BMP administration in vivo increases hepcidin expression and reduces serum iron. (Babitt, J. L., H et al. *J Clin Invest.* 117:1933-1939). Conversely, administration of soluble hemojuvelin fused to the Fc portion of human immunoglobulin Fc (HJV.Fc) in vivo, which selectively inhibits BMP-2, BMP-4, BMP-5, and BMP-6, but not BMP-7 or BMP-9, inhibits hepcidin expression, increases ferroportin expression, mobilizes reticuloendothelial cell iron stores, and increases serum iron in vivo. (Babitt, J. L., et al. 2007. *J Clin Invest.* 117: 1933-1939.) Administration of the non-selective small molecule BMP inhibitor Dorsomorphin also inhibits hepcidin expression and increases serum iron in vivo. (Yu, P. B., et al. 2008. *Nat Chem. Biol.* 4:33-41).

Hemojuvelin (also known as RGMc) is a member of the Repulsive Guidance Molecules family of proteins, including RGMa and DRAGON(RGMb), which share 50-60% amino acid identity. (Samad, T. A., et al. 2004. *J. Neurosci.* 24:2027-2036) Like Hemojuvelin, RGMa (Babitt, J. L., et al. 2005. *J. Biol. Chem.* 280:29820-29827) and DRAGON(Samad, T. A., et al. 2005. *J. Biol. Chem.* 280:14122-14129) also function as co-receptors for the BMP signaling pathway.

There is a need for a cost-effective and efficient method for regulating hepcidin expression and iron metabolism.

SUMMARY OF THE INVENTION

The present invention provides novel methods for modulating BMP-6 for treating disorders of iron overload due to hepcidin deficiency or anemia of inflammation due to hepcidin excess.

The invention relates to modulators of the BMP signaling pathway that have a role in treating disorders of iron overload due to hepcidin deficiency or anemia of inflammation due to hepcidin excess.

The present invention relates to a method for regulating iron homeostasis in a subject, said method comprising administering to said subject an effective amount of a pharmaceutical composition sufficient for modulating BMP-6 signaling at a level sufficient to alter iron homeostasis, hemoglobin levels and/or hematocrit levels in the subject. In some aspects, administering the composition reduces BMP-6 signaling. In some aspects, the composition comprises a reagent capable of binding BMP-6. In some embodiments, the reagent binds BMP-6 at residues TQSQDVARVSSASDY (SEQ ID NO:3). In some aspects, the reagent is an antibody. In some aspects, the antibody competitively inhibits BMP-6 binding by soluble human hemojuvelin protein. In certain specific embodiments, the soluble human hemojuvelin protein is HJV.Fc or HJV.His. In other aspects, the antibody inhibits BMP-6 activity by binding BMP-6 at a domain independent of the domain at which soluble human hemojuvelin protein binds BMP-6. In certain specific embodiments, the soluble human hemojuvelin protein is HJV.Fc or HJV.His.

The present invention relates to methods wherein administering the compound reduces hemojuvelin-mediated induction of hepcidin expression. In some aspects, the reagent is administered in an amount sufficient to inhibit an interaction between hemojuvelin and BMP-6. In some aspects, the reagent preferably inhibits expression or activity of human BMP-6 over BMP-2, BMP-4, BMP-5, BMP-7 or BMP-9. In some aspects, the reagent binds BMP-6 with at least 5-fold greater affinity that BMP-7.

The invention provides methods for the administration of the compositions of the instant invention which result in increased serum iron levels or increased serum transferrin saturation in the subject. The invention also provides methods for the administration of the compositions of the instant invention which result in increased hemoglobin or hematocrit levels.

The invention provides methods for the administration of the compositions of the instant invention which result in increased BMP-6 signaling. In some aspects, the composition comprises a reagent capable of increasing serum BMP-6 levels. In some aspects, the reagent increases BMP-6 expression levels.

The invention provides methods for treating a subject who has one or more symptoms of hereditary hemochromatosis, the symptoms selected from the group consisting of: increased serum iron level, increased serum transferrin saturation, reduced hepcidin expression, reduced spleen iron store, increased ferroportin expression and tissue iron overload.

The invention provides methods for administration of the composition reduces expression level of BMP-6. In some aspects the composition comprises a reagent capable of inhibiting BMP-6 gene expression, wherein the reagent is antisense DNA, siRNA, interfering RNA, microRNA (miRNA) or antisense RNA, and wherein the reduction in expression of BMP-6 is sufficient to increase serum iron level or serum transferrin saturation in the subject.

The invention provides an isolated monoclonal antibody which specifically binds to human BMP-6, wherein said human BMP-6 consists of the amino acid sequence set forth in SEQ ID NO: 1 and the binding inhibits the iron-regulating activity of BMP-6 and a composition comprising the isolated monoclonal antibody, comprising an amount of the antibody sufficient to increase serum iron level or serum transferrin saturation in a subject. In some embodiments, the isolated monoclonal antibody competitively inhibits BMP-6 binding by soluble human hemojuvelin protein to reduce binding to BMP-6 by 25%-100%. In certain specific embodiments, the soluble human hemojuvelin protein is HJV.Fc or HJV.His. In more specific embodiments, the isolated monoclonal antibody competitively inhibits BMP-6 binding by anti-BMP-6 antibodies selected from the group consisting of R & D Systems monoclonal antibody to human BMP-6, MAB507 (clone 74219), R & D systems polyclonal antibody to human BMP-6, AF507 (lot CXL04A), and Santa Cruz polyclonal antibody by 25%-100%. In other embodiments, the isolated monoclonal antibody binds BMP-6 at a domain distinct from the domain at which HJV.Fc binds.

The invention also provides anti-BMP-6 antibodies such as human antibody, consisting of a chimerized antibody, a humanized antibody, a fully human antibody, a single chain Fv fragment, a F(ab')$_2$ fragment, an Fd, a domain antibody (dAb), a diabody, a maxibody, and a nanobody. In some aspects, the isolated monoclonal antibody binds both human BMP-6 and murine BMP-6.

The invention also provides isolated nucleic acid molecules comprising a nucleotide sequence that encodes anti-BMP-6 antibody and expression vector comprising the nucleic acid molecule operably linked to a regulatory control sequence.

The invention also provides a method for using a host cell comprising said vector or a nucleic acid molecule to produce an antibody, comprising culturing said host cell under suitable conditions such that the nucleic acid is expressed to produce the antibody, is provided.

The invention also provides for treating a subject who has one or more symptoms of hereditary hemochromatosis by administration of (a) pharmaceutical composition sufficient for modulating BMP-6 signaling at a level sufficient to alter iron homeostasis, hemoglobin levels and/or hematocrit levels and (b) an erythropoiesis stimulator, in therapeutically effective amounts. Exemplary erythropoiesis stimulators include erythropoietin, erythropoietin agonist variants, and peptides or antibodies that bind and activate erythropoietin receptor. Erythropoiesis stimulators include, but are not limited to, epoetin alfa, epoetin beta, epoetin delta, epoetin omega, epoetin iota, epoetin zeta, and analogs thereof, mimetic peptides, mimetic antibodies and HIF inhibitors (see U.S. Patent Publication No. 2005/0020487, the disclosure of which is incorporated by reference in its entirety). In particular, erythropoietin includes, but is not limited to, erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,955,422 and 5,856,298; and WO 91/05867; WO 95/05465; WO 00/24893 and WO 01/81405. In certain exemplary embodiments, the erythropoiesis stimulator is selected from the group consisting of human erythropoietin and darbepoetin alfa.

The invention also provides a method for diagnosing a BMP-6-related disorder, the method comprising: (a) contacting a biological sample from a human suspected of having said disorder with an antibody that specifically binds to BMP-6 under conditions suitable for binding of the antibody to human BMP-6; and (b) quantitating the BMP-6 bound to the antibody, wherein the amount of BMP-6 in said sample, as quantitated in (b), above or below a normal level indicates the presence of a BMP-6-related disorder.

The invention also provides a method for monitoring a treatment in which a BMP-6 antagonist is administered, the method comprising: (a) contacting a biological sample, from a human that has been administered a BMP-6 antagonist, with an antibody that specifically binds to BMP-6 under conditions suitable for binding of the antibody to human BMP-6; and (b) quantitating the BMP-6 bound to the antibody, wherein a change in the amount of serum BMP-6 level, as quantitated in (b), is indicative of the efficacy of the BMP-6 antagonist. In some aspects, the antagonist is an antibody or a small molecule.

The invention also provides a method of treating a mammal with an elevated level of iron or anemia through the administration of a pharmaceutical composition that modulates BMP-6 signaling.

The invention also provides a kit for treating a disorder associated with iron homeostasis, comprising an article of manufacture comprising a vial or prefilled syringe comprising anti-BMP-6 antibodies.

The invention also provides a method for screening compounds that binds to human BMP-6 comprising contacting a candidate compound with a composition comprising bioactive BMP-6, and detecting a complex between the candidate compound and human BMP-6 in the composition, wherein detection of a complex indicates that the candidate compound binds to human BMP-6, and further wherein the candidate compound inhibits a binding of BMP-6 with HJV.Fc by at least 25%.

The invention also provides a method of generating an antibody to human BMP-6 comprising contacting an immunoglobulin producing cell with a polypeptide comprising a BMP-6 sequence of SEQ ID NO:1 or variant thereof, and isolating an immunoglobulin produced by said cell.

The invention also provides a composition for the treatment of an iron deficiency disorder comprising an antibody that specifically binds to BMP-6 and HJV.Fc. In one embodiment, the antibody competitively inhibits BMP-6 binding by soluble human hemojuvelin conjugate (HJV.Fc) protein. In another embodiment, the antibody competitively inhibits BMP-6 binding by soluble human hemojuvelin conjugate (HJV.Fc) protein. In another embodiment, the antibody binds to a domain on BMP-6 distinct from the domain to which HJV.Fc binds.

In another specific embodiment, the antibody is in an amount sufficient to reduce HJV.Fc binding to BMP-6 by 25%-100%. Preferably, the antibody is selected from the group consisting of RandD Systems monoclonal antibody, RandD systems polyclonal antibody, and Santa Cruz polyclonal antibody. In another specific embodiment, the antibody is a human antibody. In other embodiments, said antibody is selected from the group consisting of a chimerized antibody, a humanized antibody, a fully human antibody, a single chain Fv fragment, a F(ab')$_2$ fragment, an Fd, a domain antibody (dAb), a diabody, a maxibody, and a nanobody.

The invention also provides an isolated nucleic acid molecule comprising a nucleotide sequence that encodes the antibody that specifically binds to BMP-6. The invention also provides an expression vector comprising this nucleic acid molecule operably linked to a regulatory control sequence. The invention also provides a host cell comprising said vector or nucleic acid molecule.

The invention also provides a method for using the host cell disclosed herein to produce an antibody, comprising culturing the host cell of claim under suitable conditions such that the nucleic acid is expressed to produce the antibody.

The invention also provides a method for diagnosing a BMP-6-related disorder, the method comprising: contacting a biological sample from a human suspected of having said disorder with an antibody that specifically binds to BMP-6 under conditions suitable for binding of the antibody to human BMP-6; and quantitating the BMP-6 bound to the antibody, wherein the amount of BMP-6 in said sample, as quantitated in (b), above or below a normal level indicates the presence of a BMP-6-related disorder.

The invention also provides a method for monitoring a treatment in which a BMP-6 antagonist is administered, the method comprising: contacting a biological sample, from a human that has been administered a BMP-6 antagonist, an antibody that specifically binds to BMP-6 under conditions suitable for binding of the antibody to human BMP-6; and quantitating the BMP-6 bound to the antibody, wherein a change in the amount of serum BMP-6 level, as quantitated in (b), is indicative of the efficacy of the BMP-6 antagonist. In a specific embodiment, the antagonist is an antibody. In another specific embodiment, the antagonist is a small molecule.

The invention also provides an antibody that specifically binds to human BMP-6, wherein in the presence of a concentration of a peptide comprising the amino acid sequence of TQSQDVARVSSASDY (SEQ ID NO:3) the antibody is competed away from specifically binding to human BMP-6.

The invention also provides an antibody specifically binds to any 5 consecutive amino acids of TQSQDVARVSSASDY (SEQ ID NO:3). In specific embodiments, the antibody specifically binds to and 6, 7, 8, 9 or 10 consecutive amino acids of TQSQDVARVSSASDY (SEQ ID NO:3).

The present invention and other objects, features, and advantages of the present invention will become further apparent in the following Detailed Description of the Invention and the accompanying Figures and embodiments.

DETAILED DESCRIPTION OF THE INVENTION

Figure 1A:
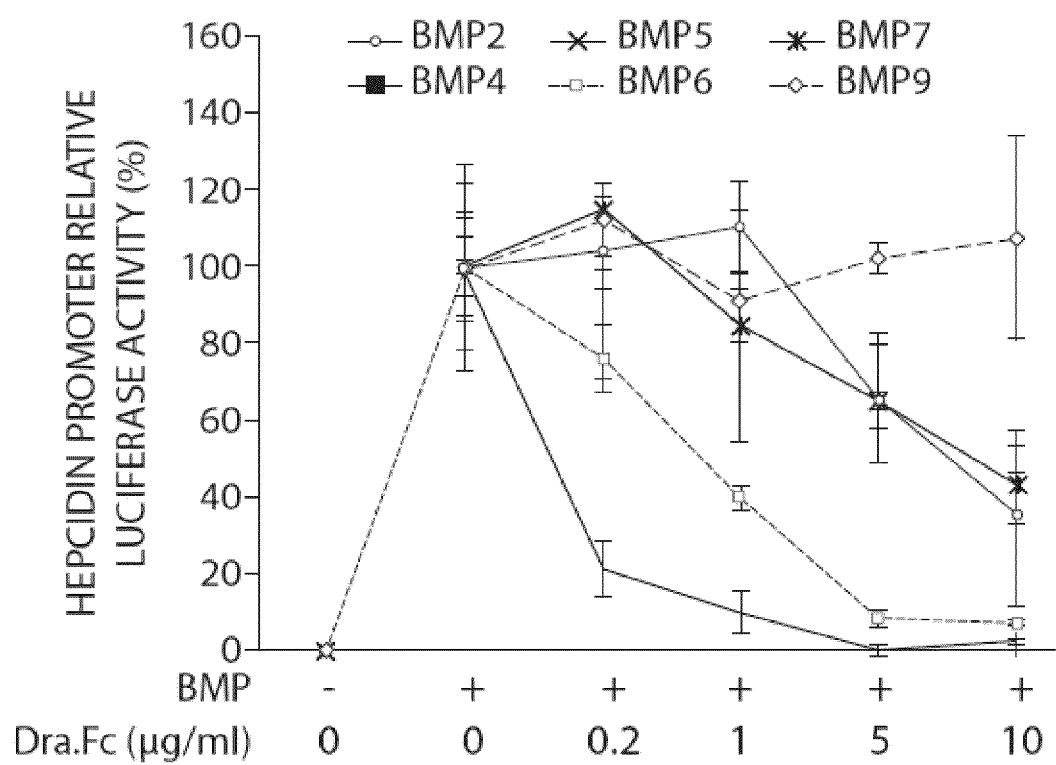
FIGS. 1A-1D show evidence that DRAGON.Fc selectively inhibits BMP induction of hepcidin expression.

The inventors surprisingly have found that BMP-6 is an important regulator of hepcidin expression and iron metabolism. Compared with soluble hemojuvelin (HJV.Fc), the homologous DRAGON.Fc fusion protein is a more potent inhibitor of hepcidin promoter activation by BMP-2 and BMP-4, but a less potent inhibitor of BMP-6 in vitro. In vivo, DRAGON.Fc has no effect on hepcidin expression and iron metabolism, while HJV.Fc or a specific neutralizing BMP-6 antibody inhibit hepcidin expression and increase serum iron. Further, Bmp6 null mice have a phenotype that resembles hereditary hemochromatosis with reduced hepcidin expression, increased ferroportin expression, increased serum iron and transferrin saturation, reduced spleen iron stores, and tissue iron overload. The inventors show that BMP-6 administration in mice increases hepcidin expression and reduces serum iron. Taken together, these data support a key role for BMP-6 as an endogenous regulator of hepcidin expression and iron metabolism in vivo.

Administration of specific neutralizing BMP-6 antibody resulted in increased serum iron and transferrin saturation indicating effects on hepcidin expression and iron metabolism. Inhibition of endogenous BMP-6 by siRNA or neutralizing antibody inhibits hemojuvelin-mediated induction of hepcidin expression. BMP-6 likely is a ligand for hemojuvelin.

Further, addition of exogenous BMP-6 was found to increase hepcidin expression and cause a dose-dependent reduction in serum iron and serum transferrin saturation.

The amino acid sequence of pro-BMP-6 is shown in Table 1 below:

TABLE 1

Amino acid sequence of human pro-BMP-6 (428 amino acids; SEQ ID NO: 1)

| 10 | 20 | 30 | 40 |
|---|---|---|---|
| DCSRQGPQRP | RSGLAPPQPP | ALRQQEEQQQ | QQQLPRGEPP |
| 50 | 60 | 70 | 80 |
| PGRLKSAPLF | MLDLYNALSA | DNDEDGASEG | ERQQSWPHEA |
| 90 | 100 | 110 | 120 |
| ASSSQRRQPP | PGAAHPLNRK | SLLAPGSGSG | GASPLTSAQD |
| 130 | 140 | 150 | 160 |
| SAFLNDADMV | MSFVNLVEYD | KEFSPRQRHH | KEFKFNLSQI |
| 170 | 180 | 190 | 200 |
| PEGEVVTAAE | FRIYKDCVMG | SFKNQTFLIS | IYQVLQEHQH |
| 210 | 220 | 230 | 240 |
| RDSDLFLLDT | RVVWASEEGW | LEFDITATSN | LWVVTPQHNM |
| 250 | 260 | 270 | 280 |
| GLQLSVVTRD | GVHVHPRAAG | LVGRDGPYDK | QPFMVAFFKV |
| 290 | 300 | 310 | 320 |
| SEVHVRTTRS | ASSRRRQQSR | NRSTQSQDVA | RVSSASDYNS |
| 330 | 340 | 350 | 360 |
| SELKTACRKH | ELYVSFQDLG | WQDWIIAPKG | YAANYCDGEC |

TABLE 1-continued

Amino acid sequence of human pro-BMP-6 (428 amino acids; SEQ ID NO: 1)

| 370 | 380 | 390 | 400 |
|---|---|---|---|
| SFPLNAHMNA | TNHAIVQTLV | HLMNPEYVPK | PCCAPTKLNA |
| 410 | 420 | | |
| ISVLYFDDNS | NVILKKYRNM | VVRACGCH | |

BMP-6 is made up of amino acids 297-428 of the pro-BMP-6 sequence shown in Table 1. BMP-6 is shown in Table 2 below.

TABLE 2

Amino acid sequence of human BMP-6 (132 amino acids; SEQ ID NO: 2)

| 10 | 20 | 30 | 40 |
|---|---|---|---|
| QQSRNRSTQS | QDVARVSSAS | DYNSSELKTA | CRKHELYVSF |
| 50 | 60 | 70 | 80 |
| QDLGWQDWII | APKGYAANYC | DGECSFPLNA | HMNATNHAIV |
| 90 | 100 | 110 | 120 |
| QTLVHLMNPE | YVPKPCCAPT | KLNAISVLYF | DDNSNVILKK |
| 130 | | | |
| YRNMVVRACG | CH | | |

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present invention:

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and αclasses are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 1-35 (H1), 50-65 (H2) and 95-102 (H3) in the $V_H$; Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the $V_L$, and 26-32 (H1), 53-55 (H2) and 96-101 (H3) in the $V_H$; Chothia and Lesk, J. Mol. Biol. 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domainantigen-binding dequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239: 1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, $Fc_\epsilon RI$.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, anti-BMP-6 antibody specifically binds to BMP-6 if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

A "mammal" for purposes of treating n infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order. In one embodiment of the invention, a combination therapy using a pharmaceutical composition sufficient for modulating BMP-6 signaling at a level sufficient to alter iron homeostasis, hemoglobin levels and/or hematocrit levels and an erythropoiesis stimulator is used. This combination is useful for treating a subject who has one or more symptoms of hereditary hemochromatosis. In various embodiments, erythropoiesis stimulators can be used to improve treatment of a patient with anemia. In particular, patients who are hypo-responsive to, including unresponsive to, erythropoiesis stimulator therapy, such as erythropoietin or analogs thereof (Epoetin alfa, Epoetin beta, darbepoetin alfa), among others, will benefit from co-treatment with a hepcidin activity antagonist or hepcidin expression inhibitor.

As used herein, "erythropoiesis stimulator" means a chemical compound that directly or indirectly causes activation of the erythropoietin receptor, for example, by binding to and causing dimerization of the receptor or by stimulating endogenous erythropoietin expression. Erythropoiesis stimulators include erythropoietin and variants, analogs, or derivatives thereof that bind to and activate erythropoietin receptor; antibodies that bind to erythropoietin receptor and activate the receptor; or peptides that bind to and activate erythropoietin receptor; or small organic chemical compounds, optionally less than about 1000 Daltons in molecular weight, that bind to and activate erythropoietin receptor. Erythropoiesis stimulators include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), mimetic antibodies and HIF inhibitors (see U.S. Patent Publication No. 2005/0020487, the disclosure of which is incorporated by reference in its entirety). Exemplary erythropoiesis stimulators include erythropoietin, darbepoetin, erythropoietin agonist variants, and peptides or antibodies that bind and activate erythropoietin receptor (and include compounds reported in U.S. Patent Application Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; 7,217,689; PCT publication nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and US publication nos. US 2002/0155998; US 2003/0077753; US 2003/0082749; US 2003/0143202; US 2004/0009902; US 2004/0071694; US 2004/0091961; US 2004/0143857; US 2004/0157293; US 2004/0175379; US 2004/0175824; US 2004/0229318; US 2004/0248815; US 2004/0266690; US 2005/0019914; US 2005/0026834; US 2005/0096461; US 2005/0107297; US 2005/0107591; US 2005/0124045; US 2005/0124564; US 2005/0137329; US 2005/0142642; US 2005/0143292; US 2005/0153879; US 2005/0158822; US 2005/0158832; US 2005/0170457; US 2005/0181359; US 2005/0181482; US 2005/0192211; US 2005/0202538; US 2005/0227289; US 2005/0244409; US 2006/0088906; US 2006/0111279.

Exemplary sequences, manufacture, purification and use of recombinant human erythropoietin are described in a number of patent publications, including but not limited to Lin U.S. Pat. No. 4,703,008 and Lai et al. U.S. Pat. No. 4,667,016, each of which is incorporated herein by reference in its entirety. Darbepoetin is a hyperglycosylated erythropoietin analog having five changes in the amino acid sequence of rHuEPO which provide for two additional carbohydrate chains. More specifically, darbepoetin alfa contains two additional N-linked carbohydrate chains at amino acid residues 30 and 88. Exemplary sequences, manufacture, purification and use of darbepoetin and other erythropoietin analogs are described in a number of patent publications, including Strickland et al., 91/05867, Elliott et al., WO 95/05465, Egrie et al., WO 00/24893, and Egrie et al. WO 01/81405, each of which is incorporated herein by reference in its entirety. Derivatives of naturally occurring or analog polypeptides include those which have been chemically modified, for example, to attach water soluble polymers (e.g., pegylated), radionuclides, or other diagnostic or targeting or therapeutic moieties.

The term "erythropoietic activity" means activity to stimulate erythropoiesis as demonstrated in an in vivo assay, for example, the exhypoxic polycythemic mouse assay. See, e.g., Cotes and Bangham, Nature 191:1065 (1961).

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™

"Label" as used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "epitope tagged" as used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The terms "nucleic acid" and "polynucleotide" are used interchangeably herein to refer to single- or double-stranded RNA, DNA, PNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or Influenza A-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

The present invention includes human BMP-6 antibodies comprising a polypeptide of the present invention, including those polypeptides encoded by a polynucleotide sequence corresponding to Bmp6, and fragments and variants thereof. In particular embodiments, the antibodies of the present invention bind to the BMP-6 protein. In certain embodiments, the present invention provides BMP-6 antibodies that bind to epitopes within BMP-6 that are only present in the native conformation, i.e., as expressed in cells.

As will be understood by the skilled artisan, general description of antibodies herein and methods of preparing and using the same also apply to individual antibody polypeptide constituents and antibody fragments.

The antibodies of the present invention may be polyclonal or monoclonal antibodies. However, in preferred embodiments, they are monoclonal. In particular embodiments, antibodies of the present invention are fully human antibodies. Methods of producing polyclonal and monoclonal antibodies are known in the art and described generally, e.g., in U.S. Pat. No. 6,824,780. Typically, the antibodies of the present invention are produced recombinantly, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germline mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or PRIMATIZED™. In practice, humanized antibodies are typically human antibodies in which some hypervariable region residues and possibly some FR residues are substituted by residues from analogous sites in rodent antibodies.

In the context of the present invention, chimeric antibodies also include fully human antibodies wherein the human hypervariable region or one or more CDRs are retained, but one or more other regions of sequence have been replaced by corresponding sequences from a non-human animal.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a $\gamma$, $\mu$, $\alpha$, $\delta$, or $\epsilon$ heavy chain. A $\gamma$ chain may be $\gamma1$, $\gamma2$, $\gamma3$, or $\gamma4$; and an $\alpha$ chain may be $\alpha1$ or $\alpha2$.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well; IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils an mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

In various embodiments, antibodies of the present invention, and fragments thereof, comprise a variable light chain that is either $\kappa$ or $\lambda$. The $\lambda$ chain may be any of subtype, including, e.g., $\lambda1$, $\lambda2$, $\lambda3$, and $\lambda4$.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')$_2$ and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641, 870 for example. Such linear antibody fragments may be monospecific or bispecific. Antibodies of the present invention further include single chain antibodies.

Amino acid sequence modification(s) of the antibodies described herein are contemplated. For example, it may be desirable to improve the binding affinity and/or other biological properties of the antibody. Amino acid sequence variants of the antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics. The amino acid changes also may alter post-translational processes of the antibody, such as changing the number or position of glycosylation sites. Any of the variations and modifications described above for polypeptides of the present invention may be included in antibodies of the present invention. A useful method for identification of certain residues or regions of an antibody that are preferred locations for mutagenesis is called "alanine scanning mutagenesis" as described by Cunningham and Wells in Science, 244:1081-1085 (1989).

Methods of identifying antibodies or specific binding agents which bind BMP-6 and/or which cross-block soluble HJV.Fc or exemplary antibodies described herein, and/or which inhibit BMP-6 activity are also provided. Such methods may utilize the composition of highly purified, bioactive, human BMP-6 (either chemically synthesized or produced in bacteria or non-mammalian cells) provided herein.

Antibodies or specific binding agents may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

To initially screen for antibodies or specific binding agents which bind to the desired epitope on the target antigen, a routine cross-blocking assay such as that described in Antibodies, A Laboratory Manual, Cold Spring Harbor Laboratory, Ed Harlow and David Lane (1988), can be performed. Routine competitive binding assays may also be used, in which the unknown antibody is characterized by its ability to inhibit binding of target to a target-specific antibody of the invention. Intact antigen, fragments thereof such as the extracellular domain, or linear epitopes can be used. Epitope mapping is described in Champe et al., J. Biol. Chem. 270: 1388-1394 (1995).

In one variation of an in vitro binding assay, the invention provides a method comprising (a) contacting an immobilized BMP-6 with a candidate antibody or specific binding agent and (b) detecting binding of the candidate antibody or specific binding agent to the BMP-6. In an alternative embodiment, the candidate antibody or specific binding agent is immobilized and binding of BMP-6 is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

In some embodiments, antibodies or specific binding agents that inhibit or neutralize human BMP-6 activity may be identified by contacting BMP-6 with the antibody (or specific binding agent), comparing BMP-6 activity in the presence and absence of the test antibody (or specific binding agent), and determining whether the presence of the antibody (or specific binding agent) decreases activity of the BMP-6. The biological activity of a particular antibody, or specific binding agent, or combination of antibodies or specific binding agents, may be evaluated in vivo using a suitable animal model, including any of those described herein.

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

Hemojuvelin (also known as RGMc) is a member of the Repulsive Guidance Molecules family of proteins, including RGMa and DRAGON(RGMb), which share 50-60% amino acid identity. (Samad, T. A., et al. 2004. *J. Neurosci.* 24:2027-2036). Like Hemojuvelin, RGMa (Babitt, J. L., et al. 2005. *J. Biol. Chem.* 280:29820-29827) and DRAGON(Samad, T. A., et al. 2005. *J. Biol. Chem.* 280:14122-14129) also function as co-receptors for the BMP signaling pathway.

Figure 1B:
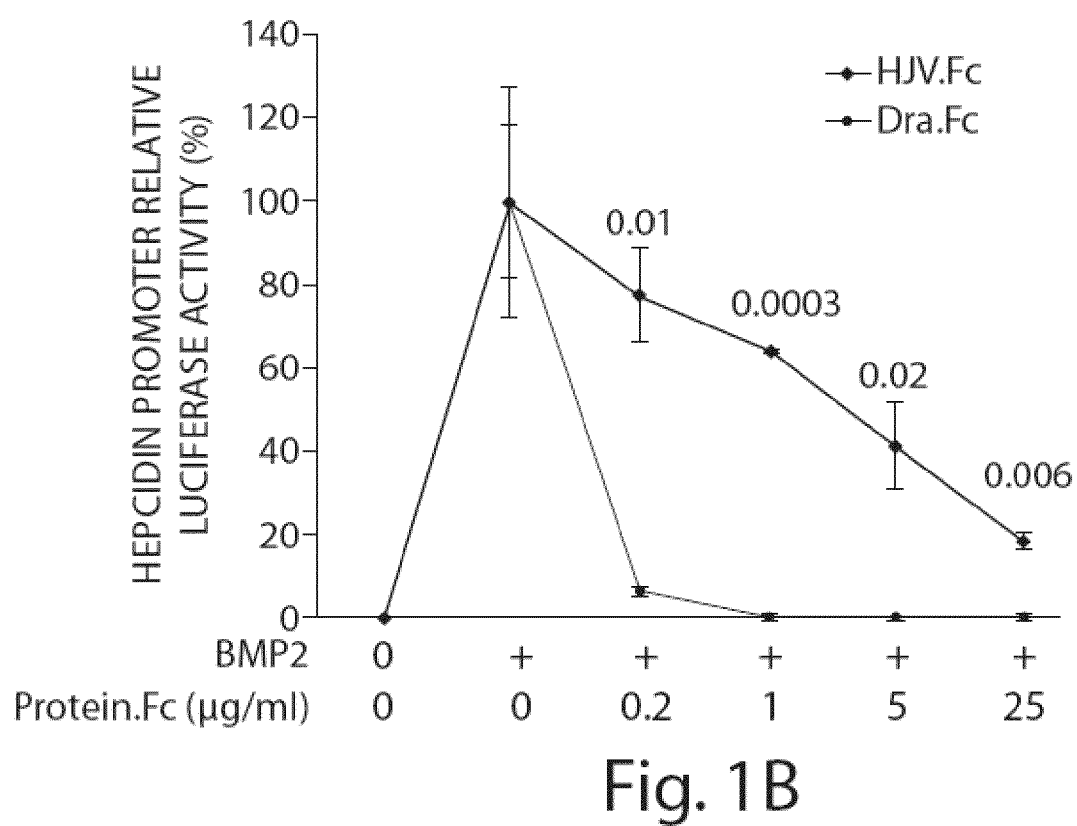
Figure 1C:
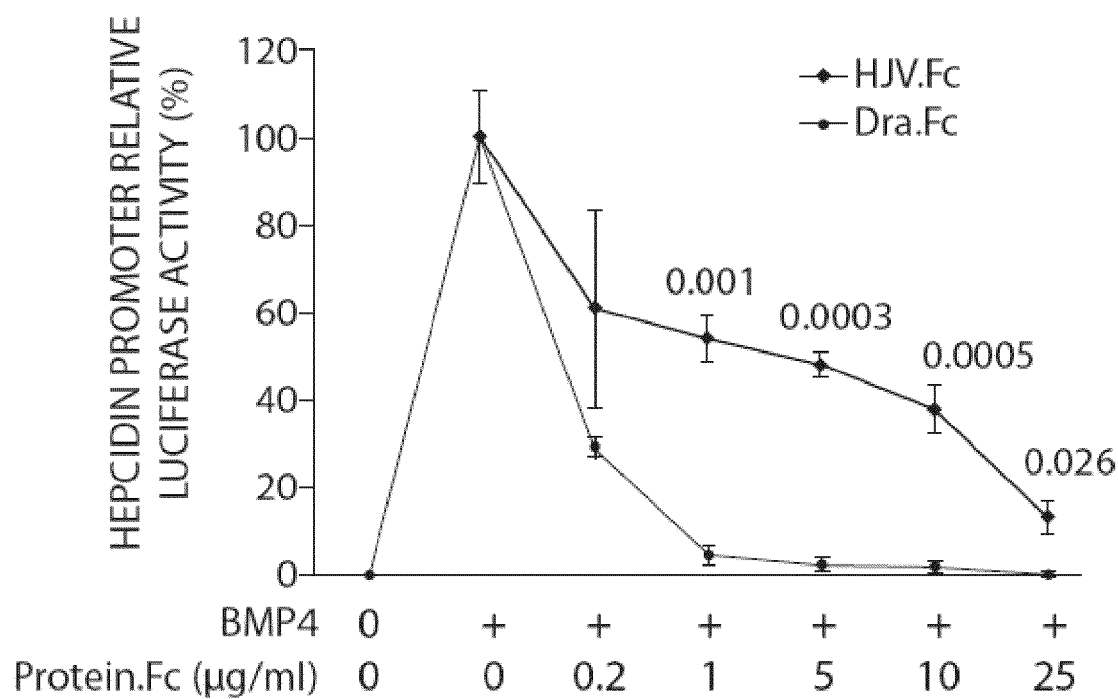
Figure 1D:
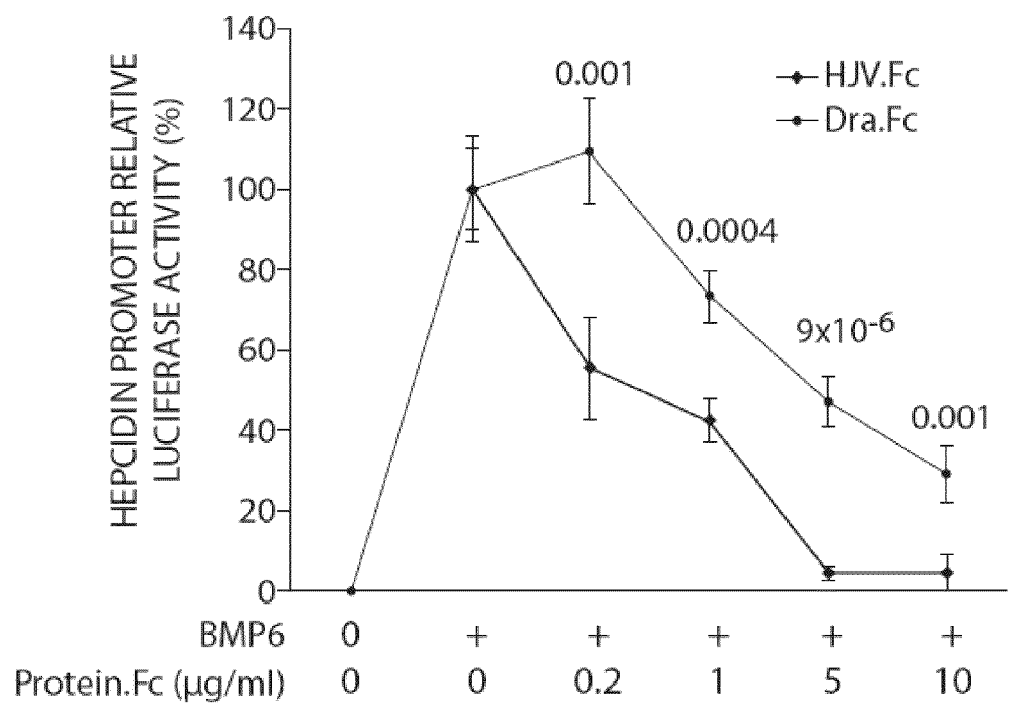

Other BMP inhibitors may function as potential therapy for anemia due to hepcidin excess. Whether purified soluble DRAGON fused to the Fc portion of human immunoglobulin Fc (DRAGON.Fc) inhibited BMP induction of hepcidin expression in a manner similar to HJV.Fc (Babitt, J. L., et al. 2007. *J Clin Invest*. 117:1933-1939) was tested. Hep3B cells were transfected with a hepcidin promoter firefly luciferase reporter and a control Renilla luciferase vector. Cells were stimulated with various BMP ligands, either alone or in combination with increasing concentrations of DRAGON.Fc. As shown in FIG. 1A, DRAGON.Fc significantly inhibited hepcidin promoter induction in response to BMP-2 and BMP-4, but was less effective in inhibiting BMP-5, BMP-6, and BMP-7 and did not inhibit BMP-9. In comparison with HJV.Fc, DRAGON.Fc was significantly more potent against BMP-2 (FIG. 1B) and BMP-4 (FIG. 1C), but was less potent against BMP-6 (Fig 1D). DRAGON.Fc also inhibited endogenous hepcidin mRNA expression in hepatoma-derived HepG2 cells, where basal hepcidin expression is dependent in part on endogenous BMP-2, BMP-4, and BMP-6 ligands (data not shown; Babitt, J. L., et al. 2007. *J Clin Invest*. 117:1933-1939).

Whether administration of DRAGON.Fc in mice affected hepcidin expression and iron metabolism was tested. DRAGON.Fc had no effect on hepatic hepcidin expression as measured by quantitative real-time RT-PCR (FIG. 2A), splenic ferroportin expression as measured by Western blot (FIG. 2B), serum iron (FIG. 2C), serum transferring saturation (FIG. 2D), liver iron content (FIG. 2E), or spleen iron content (FIG. 2F) compared with mock treated control mice. An equivalent dose of HJV.Fc reduced hepatic hepcidin expression (FIG. 2A), increased splenic ferroportin expression (FIG. 2B), increased serum iron (FIG. 2C) and transferrin saturation (FIG. 2D), increased liver iron content (FIG. 2E) and reduced spleen iron content (FIG. 2F) compared with mock treated control mice. To confirm that sufficient active DRAGON.Fc was present in the serum of mice injected with DRAGON.Fc protein to inhibit BMP-2, we tested the ability of serum from these mice to inhibit BMP-2 induction of hepcidin promoter activity as measured by luciferase assay. Serum from mock treated control mice inhibited BMP-2 induction of hepcidin promoter activity by about 30% (FIG. 2G, compare bars 3 to 2), likely due to the presence of known secreted BMP inhibitors such as Noggin (23). Serum from DRAGON.Fc treated mice was significantly more potent compared with serum from mock treated control mice, inhibiting BMP-2 induction of hepcidin promoter activity by over 70% (FIG. 2G, bar 4).

Since DRAGON.Fc had no effect on hepcidin expression and iron metabolism in vivo despite its higher potency in vitro as an inhibitor of BMP-2 and BMP-4 compared with HJV.Fc, while DRAGON.Fc was less potent at inhibiting BMP-6 compared with HJV.Fc, BMP-6 may be an important endogenous regulator of hepcidin expression and iron metabolism. Whether administration of a specific neutralizing BMP-6 antibody affected hepcidin expression and iron metabolism in mice was tested. As shown in FIG. 3A, the BMP-6 neutralizing antibody selectively inhibited BMP-6 activation of the hepcidin promoter luciferase reporter in Hep3B cells, but had no significant effect on BMP-2, BMP-4, BMP-5, or BMP-9. The BMP-6 antibody exhibited some inhibitory activity against BMP-7 at higher concentrations, but significantly less compared with BMP-6 (FIG. 3A). As shown in FIG. 3B, mice treated with BMP-6 antibody for three days had significantly reduced hepatic hepcidin expression by about 50% compared with mock treated control mice as measured by quantitative real-time RT-PCR. Additionally, BMP-6 antibody treated mice had significantly increased serum iron and transferrin saturation compared with mock treated controls (FIGS. 3C and D).

Figure 4A:
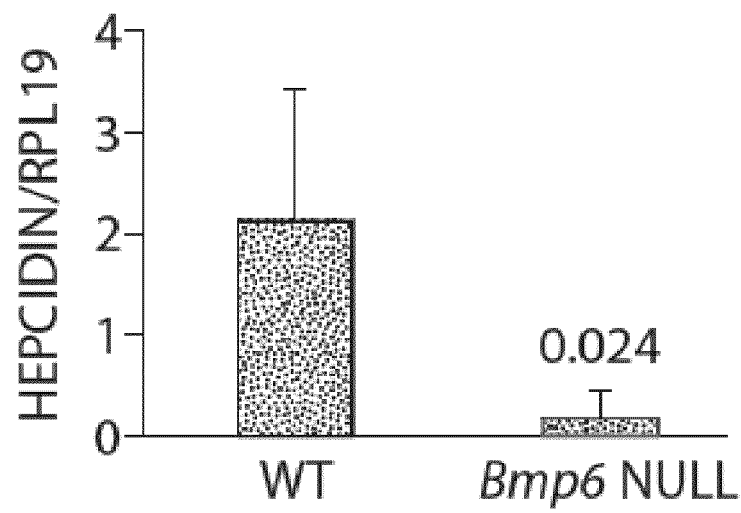
FIGS. 4A-4H show evidence that Bmp6 null mice exhibit reduced hepatic hepcidin expression, increased spleen ferroportin expression, increased serum iron and transferrin saturation, increased liver iron content and reduced spleen iron content.
Figure 4B:
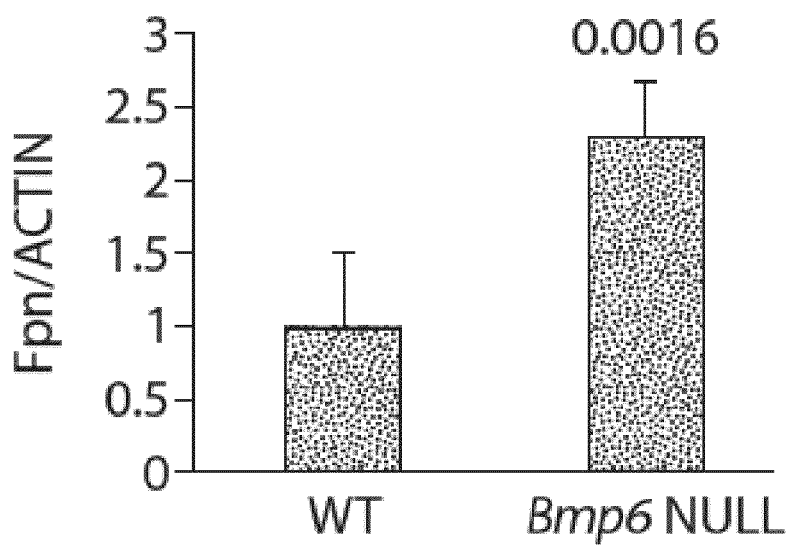
Figure 4C:
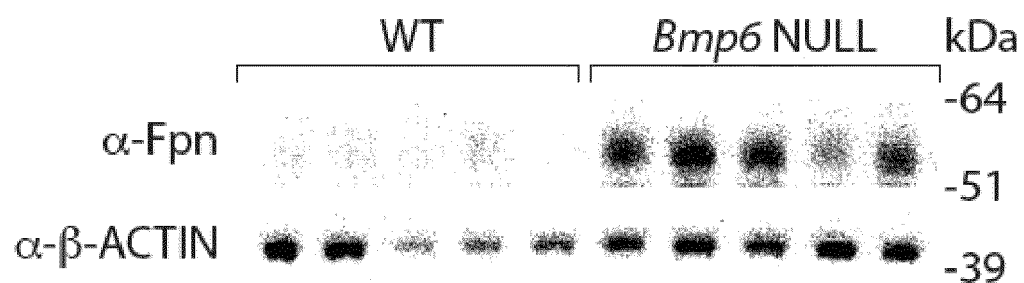
Figure 4D:
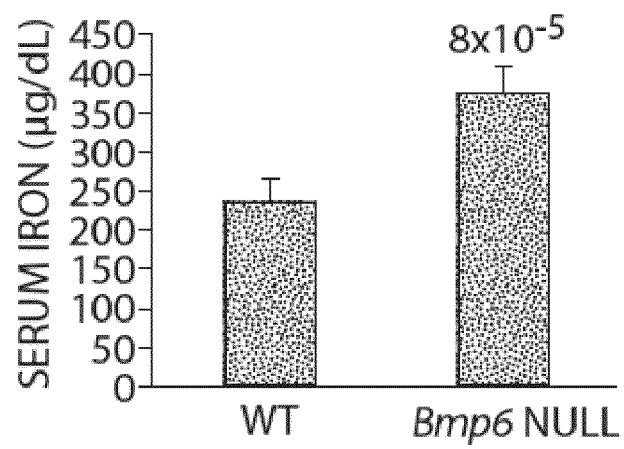
Figure 4E:
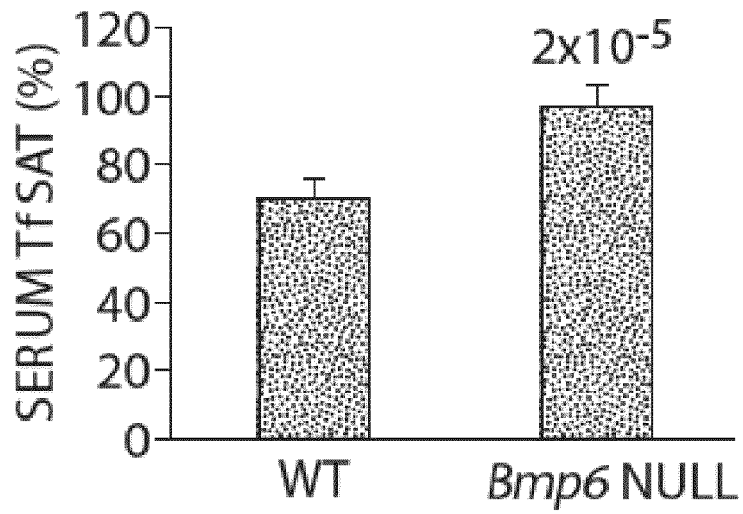
Figure 4F:
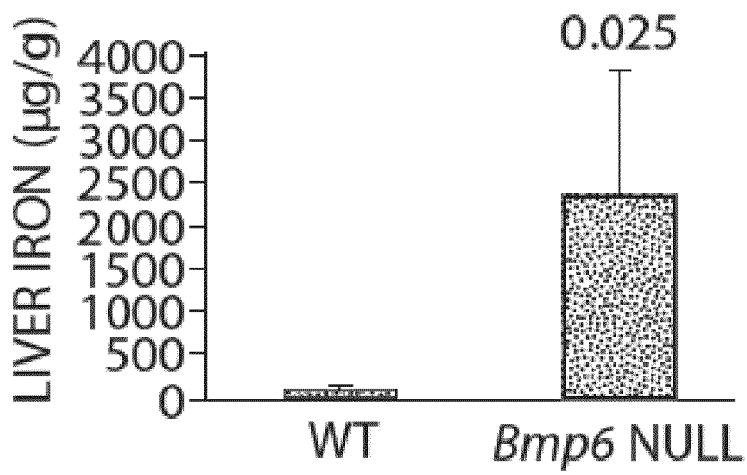
Figure 4G:
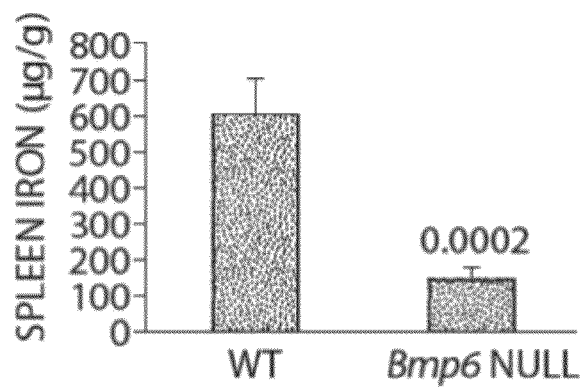
Figure 4H:
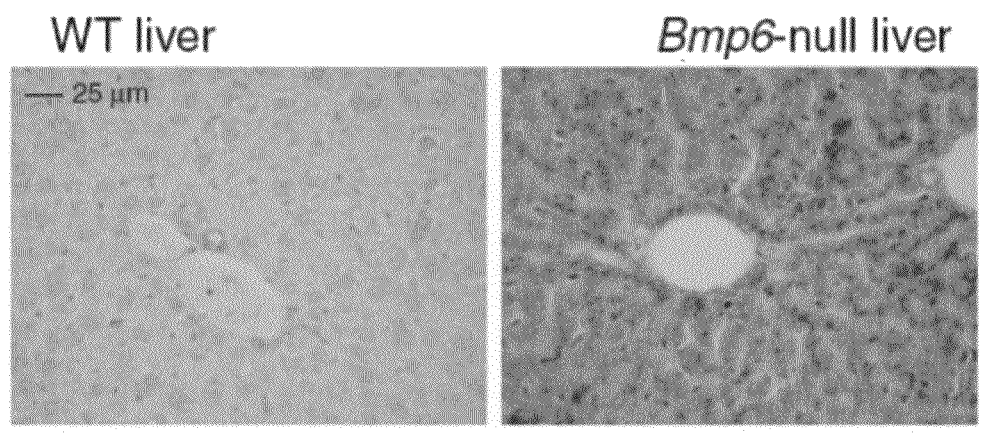

The importance of endogenous BMP-6 in regulating hepcidin expression and iron metabolism, was confirmed by testing in 8 week-old Bmp6 null mice, which were previously generated by Solloway et al. (Solloway M J, et al. 1998. *Dev Genet.* 22:321-39). These Bmp6 null mice were described to have some mild delays in bone formation during development, but no other overt defects were Compared with wild-type control mice, Bmp6 null mice exhibited reduced hepatic hepcidin expression by approximately 10-fold as measured by quantitative real-time RTPCR (FIG. 4A), and increased splenic ferroportin expression by 2.3-fold as measured by Western blot (FIGS. 4B and C). Additionally, Bmp6 null mice had significantly increased serum iron with serum transferrin saturation approaching 100% (FIGS. 4D and E). Liver iron content was increased over 20-fold (FIGS. 4F and H), while spleen iron content was reduced by 4-fold (FIG. 4G) in Bmp6 null mice compared with wildtype controls. The degree of iron overload in the liver of 8 week-old Bmp6 null mice appears comparable to that reported in Hfe2-I mice at a similar age. (Huang, F. W., et al. *J. Clin. Invest.* 115:2187-2191; Niederkofler, V., Salie, R., Arber, S. 2005. *J Clin Invest.* 115:2180-6). Thus, Bmp6 null mice have a phenotype that resembles juvenile hemochromatosis due to loss of the BMP co-receptor hemojuvelin.

Next, the ability of exogenous BMP-6 to regulate hepcidin expression and iron metabolism in vivo was tested. Mice were injected with a single dose of exogenous BMP-6 ligand at 250 and 1000 μg/kg IP. BMP-6 administration significantly increased hepatic hepcidin expression, as measured by quantitative real-time RT-PCR. BMP-6 administration also caused a dose dependent reduction in serum iron (FIG. 5B) and serum transferrin saturation (FIG. 5C).

These results demonstrate that exogenous BMP-6 administration in vivo positively regulates hepcidin expression and reduces serum iron, while knockout of the Bmp6 gene or selective inhibition of endogenous BMP-6 using a BMP-6 antibody inhibits hepcidin expression, increase serum iron, and ultimately results in a phenotype resembling hereditary hemochromatosis due to mutations in the BMP co-receptor Hfe2. These data support the importance of BMP-6 as a major endogenous regulator of hepcidin expression.

Numerous BMP ligands have been shown to regulate hepcidin in vitro, including BMP-2, BMP-4, BMP-5, BMP-6, BMP-7, and BMP-9 (Babitt, J. L., et al. 2006. *Nat. Genet.* 38:531-539; Babitt, J. L., et al. 2007. *J Clin Invest.* 117:1933-1939; Wang, R. H., et al. 2005. *Cell Metab.* 2:399-409; Truksa, J., et al. 2006. *Proc. Natl. Acad. Sci. USA.* 103:10289-10293). Messenger RNA for all of these ligands, excluding BMP-7, is expressed endogenously in human liver (Xia Y, et al. 2008. *Blood.* 1115 195-204). Although it previously has been shown that hemojuvelin binds directly to BMP-2 and BMP-4 ligands (Babitt, J. L., et al. 2006. *Nat. Genet.* 38:531-539), a soluble version of hemojuvelin, HJV.Fc, inhibits BMP-6 activation of hepcidin activity even more potently than its ability to inhibit BMP-2 and BMP-4 activity (Babitt, J. L., et al. 2007. *J Clin Invest.* 117:1933-1939). Additionally, inhibition of endogenous BMP-6 by siRNA or a neutralizing antibody inhibits hemojuvelin-mediated induction of hepcidin expression (Xia Y, et al. 2008. *Blood.* 1115 195-204). These data suggest that BMP-6 is a ligand for hemojuvelin.

Further support for a role for BMP-6 in iron metabolism comes from a recent study reporting that Bmp6 transcripts were increased in response to an iron enriched diet and reduced in response to an iron poor diet (Kautz, L., et al. 2008. *Blood.* 112:1503-9). Bmp2 transcripts were up-regulated lightly under extreme iron overload in that study and Bmp4 was not altered (Id.). Although hemojuvelin does bind to both BMP-2 and BMP-4, the inability of DRAGON.Fc, which selectively inhibits BMP-2 and BMP-4, to inhibit hepcidin expression and modulate systemic iron balance in our study suggests that BMP-2 and BMP-4 ligands may be less important in this context. Tests by the inventors also did not find any changes in Bmp2 and Bmp4 transcript levels in the liver of Bmp6 null mice despite significant iron overload (data not shown). However, the data does not definitively rule out any possible role for other BMP ligands, including BMP-2 and BMP-4, in iron metabolism.

The data clearly suggests that selective BMP-6 inhibitors may be effective agents for treating anemia of inflammation due to hepcidin excess. The lack of any other notable phenotype in Bmp6 null mice suggest that a more selective inhibitor may be better tolerated with fewer off-target effects. Additionally, BMP-6-like agonists may be an alternative treatment strategy for managing iron overload disorders in patients resistant to current therapies. Although no human patients with BMP-6 mutations have yet been described, the data also suggests that BMP-6 mutations or BMP-6 gene variants may function as another cause of hereditary hemochromatosis or a modifier of disease penetrance.

Without further elaboration, it is believed that one skilled in the art can, using the preceding description, utilize the present invention to its fullest extent. The following examples are illustrative only, and not limiting of the remainder of the disclosure in any way whatsoever.

EXAMPLES

Example 1

Preparation of cDNA cDNA encoding codon optimized DRAGON.Fc was generated by GenScript Corporation (Piscataway, N.J. 08854), based on the human DRAGON protein sequence upstream of the predicted GPI anchor (UniProtKB/Swiss-Prot accession Q6NW40, amino acids 1-409) and the human IgG1 Fc sequence (from the Signal pIg plus vector (R&D Systems) and GenBank AF150959).

Example 2

Production and Purification of DRAGON.Fc and HJV.Fc.

cDNA encoding DRAGON.Fc was transfected using 293fectin (Invitrogen) into Freestyle 293-F cells (Invitrogen)

according to the manufacturer's instructions. Transfected cells were cultured in GIBCO Freestyle 293 Expression medium (Invitrogen) shaking at 110 RPM in a humidified 8% $CO_2$ incubator at 37° C. Seven days after transfection, cells were pelleted by centrifugation and DRAGON.Fc was purified from the media via one-step Protein A affinity chromatography using Hi-Trap rProtein A FF columns (Amersham Biosciences) as described in Babbitt, J. L., et al. 2005. J. Biol. Chem. 280:29820-29827. HJV.Fc was produced as described in Babitt, J. L., et al. 2007. J Clin Invest. 117:1933-9. To determine purity and to quantify protein concentration, DRAGON.Fc and HJV.Fc were subjected to reducing SDS-PAGE followed by Bio-safe Coomassie blue staining (Bio-Rad) as well as Western blot with anti-HJV antibody (Babitt, J. L., et al. 2006. Nat. Genet. 38:531-539), anti-DRAGON antibody (Samad, T. A., et al. 2004. J. Neurosci. 24:2027-2036), and goat anti-human Fc antibody (Jackson ImmunoResearch Laboratories) as described. (Babitt, J. L., et al. 2006. Nat. Genet. 38:531-539; Samad, T. A., et al. 2004. J. Neurosci. 24:2027-2036). Protein concentration was also quantified by the bovine serum albumin protein assay (Pierce).

Example 3

Production of BMP-6

Purified recombinant human BMP-6 was prepared as previously described. (Simic, P., et a/0.2006. J Biol. Chem. 281:25509-21). Lyophilized BMP-6 was dissolved in 20 mM sodium acetate, 5% mannitol solution, pH 4.0 for animal injections.

Example 4

Luciferase Assay

Hepcidin promoter luciferase reporter assays in hepatoma-derived Hep3B cells were carried out using the Dual-Luciferase Reporter Assay System (Promega) as previously described (Babitt, J. L., et al. 2006. Nat. Genet. 38:531-539; Babitt, J. L., et al. 2007. J Clin Invest. 117:1933-9) with the following modifications. Hep3B cells transfected with the hepcidin promoter luciferase reporter (Babitt, J. L., et al. 2006. Nat. Genet. 38:531-539) and control Renilla luciferase vector (pRL-TK) were serum starved in a-MEM with L-glutamine (Invitrogen) supplemented with 1% FBS for 6 hours, followed by stimulation with 25 ng/mL BMP-2 kindly provided by Vicki Rosen, Harvard School of Dental Medicine), BMP-4, BMP-6, or BMP-7, 50 ng/mL BMP-5 or 5 ng/mL BMP-9 (R&D Systems) either alone or with 0.2-25 µg/mL of DRAGON.Fc, HJV.Fc or anti-BMP-6 antibody for 16 hrs. Relative concentrations of BMP ligands were chosen to elicit similar degrees of hepcidin promoter luciferase activity, as previously described (Babitt, J. L., et al. 2007. J Clin Invest. 117:1933-9).

Example 5

Animals

All animal protocols were approved by the Institutional Animal Care and Use Committee at the Massachusetts General Hospital and the Institutional Animal Care Committee and the Ministry of Science and Technology at the University of Zagreb School of Medicine. Eight-week-old 12956/SvEvTac mice (Taconic) were housed in the Massachusetts General Hospital rodent facility and fed on the Prolab 5P75 Isopro RMH 3000 diet with 380 parts per million iron. Bmp6 null mice on a mixed 129Sv/C57 background (Solloway M J, et al. 1998. Dev Genet. 22:321-39) kindly provided by Elizabeth J. Robertson, were housed at the University of Zagreb School of Medicine and maintained on standard GLP diet (4RF21, Mucedola, Italy) with 180 mg/kg iron.

For DRAGON.Fc and HJV.Fc experiments, 8-week-old 12956/SvEvTac mice (Taconic) received an intraperitoneal injection of DRAGON.Fc at doses of 5 or 10 mg/kg, HJV.Fc at doses of 5 or 7 mg/kg, or an equal volume of isotonic saline three times per week for three weeks. For BMP-6 antibody injection experiments, 8-week-old 129S6/SvEvTac mice received an intraperitoneal injection of monoclonal anti-human BMP-6 antibody (R&D Systems) at 10 mg/kg or isotonic saline daily for three days. Twelve hours after the last injection, mice were sacrificed and blood and livers were harvested for measurement of iron parameters and hepcidin expression.

For BMP-6 injection experiments, 8-week-old 12956/SvEvTac mice received an intraperitoneal injection of BMP-6 at 250 or 1000 mcg/kg or an equal volume of vehicle alone (20 mM sodium acetate, 5% mannitol solution, pH 4.0). Six hours after injection, mice were sacrificed and blood, livers, and spleen were harvested for measurement of iron parameters and hepcidin expression.

For Bmp6 null mouse experiments, five 8-week-old Bmp6 null mice and five wildtype control mice were sacrificed and blood, livers, and spleen were harvested for measurements of iron parameters and hepcidin expression.

Example 6

Quantitative Real-time RT-PCR

Total RNA was isolated from mouse livers using the RNeasy kit (QIAGEN) according to the manufacturer's instructions. Real-time quantification of Hampl mRNA transcripts relative to RPL19 was performed using 2-step quantitative real-time RT-PCR as previously described. (Babitt, J. L., et al. 2006. Nat. Genet. 38:531-539; Babitt, J. L., et al. 2007. J Clin Invest. 117:1933-9; Xia, Y., et al. 2007. J Biol. Chem. 282:18129-40). Real time quantification of Bmp2, Bmp4, and Bmp6 mRNA from livers of Bmp6 null versus wildtype mice was also performed using previously described primers (Kautz, L., et al. 2008. Blood. 112:1503-9).

Example 7

Western Blot

For ferroportin assays, spleen membrane preparations were prepared as previously described. Protein concentrations were determined by BCA assay (Pierce). After solubilization in 1× Laemmli buffer for 30 minutes at room temperature, 20 µg of protein per sample were resolved by SDS-PAGE using pre-cast NuPAGE Novex 4-12% Bis-Tris gels (Invitrogen) and transferred onto PDVF membranes (liquid transfer method). The blots were saturated with 10% non-fat milk in tris buffered saline (TBS) containing 0.1% Tween (TBS-T) and probed overnight at 4° C. with 2.5 µg/ml ferroportin antibody (diluted in TBS-T with 5% non-fat milk). Knutson, M. D., et al. 2005. Proc Natl Acad Sci USA 0.102:1324-8. Following wash with TBS-T, the blots were incubated with 1:5000 diluted peroxidase-coupled goat anti-rabbit IgG (Sigma) for 1 hour. Detection was performed with the enhanced chemiluminescence ECLB method (Perkin Elmer). Blots were stripped and re-probed for β-actin expression as a loading control as described in Babitt, J. L., et al. 2006. *Nat. Genet.* 38:531-539. Chemiluminescence was quantitated using IPLab Spectrum software version 3.9.5 r2 (Scanalytics).

Example 8

Serum and Tissue Iron Measurements

Serum was collected and analyzed for iron concentration and unsaturated iron-binding capacity as previously described. Total iron binding capacity and transferrin saturation were calculated as previously described. Quantitative measures of nonheme iron was performed on liver and spleen tissue as previously described. (See Babitt, J. L., et al. 2007. *J Clin Invest.* 117:1933-9).

Example 9

Histology

Livers from Bmp6 null and wildtype mice were fixed in 2% paraformaldehyde followed by 2% ethanol and embedded in paraffin. Sections at 5 pm were deparaffinized in Xylene and hydrated to distilled water. Sections were then placed in staining solution with equal volumes of 2% potassium ferrocyanide (Electron Microscopy Sciences, Hatfield, Pa.) and 2% hydrochloric acid, for 60 min at room temperature. The sections were then rinsed in distilled water, counterstained in Safranin 0.2% (Electron Microscopy Sciences, Hatfield, Pa.) for 2 min, and washed in 1% acetic acid, before being dehydrated in 95% alcohol, absolute alcohol, cleared in Xylene, and mounted in DPX.

Example 10

Statistics

A two-tailed Student's t test with P<0.05 was used to determine statistical significance.

Example 11

DRAGON.Fc Selectively Inhibits BMP Induction of Hepcidin Expression

FIG. 1. Hep3B cells were transfected with a hepcidin promoter luciferase reporter and control Renilla luciferase vector (pRL-TK). Forty-eight hours after transfection, cells were incubated in the absence or presence of BMP-2, BMP-4, BMP-5, BMP-6, BMP-7, or BMP-9 ligands, either alone or in combination with 0.2 to 25 μg/mL purified DRAGON.Fc (Dra.Fc) or HJV.Fc for 16 hours as shown. Cell lysates were assayed for luciferase activity and relative luciferase activity was calculated as the ratio of firefly to Renilla luciferase to control for transfection efficiency. Results are reported as the mean+/−s.d. of the percent decrease in relative luciferase activity for cells treated with BMP ligands in combination with DRAGON.Fc or HJV.Fc compared with cells treated with BMP ligands alone, n=2 to 4 per group. Exact P-values are shown. (1A) Effects of DRAGON.Fc on BMP-2, BMP-4, BMP-5, BMP-6, BMP-7, and BMP-9 ligands. (1B-1D). Head to head comparison of DRAGON.Fc and HJV.Fc for inhibiting BMP-2 (1B), BMP-4 (1C) and BMP-6 (1D) are shown.

Example 12

Figure 2:
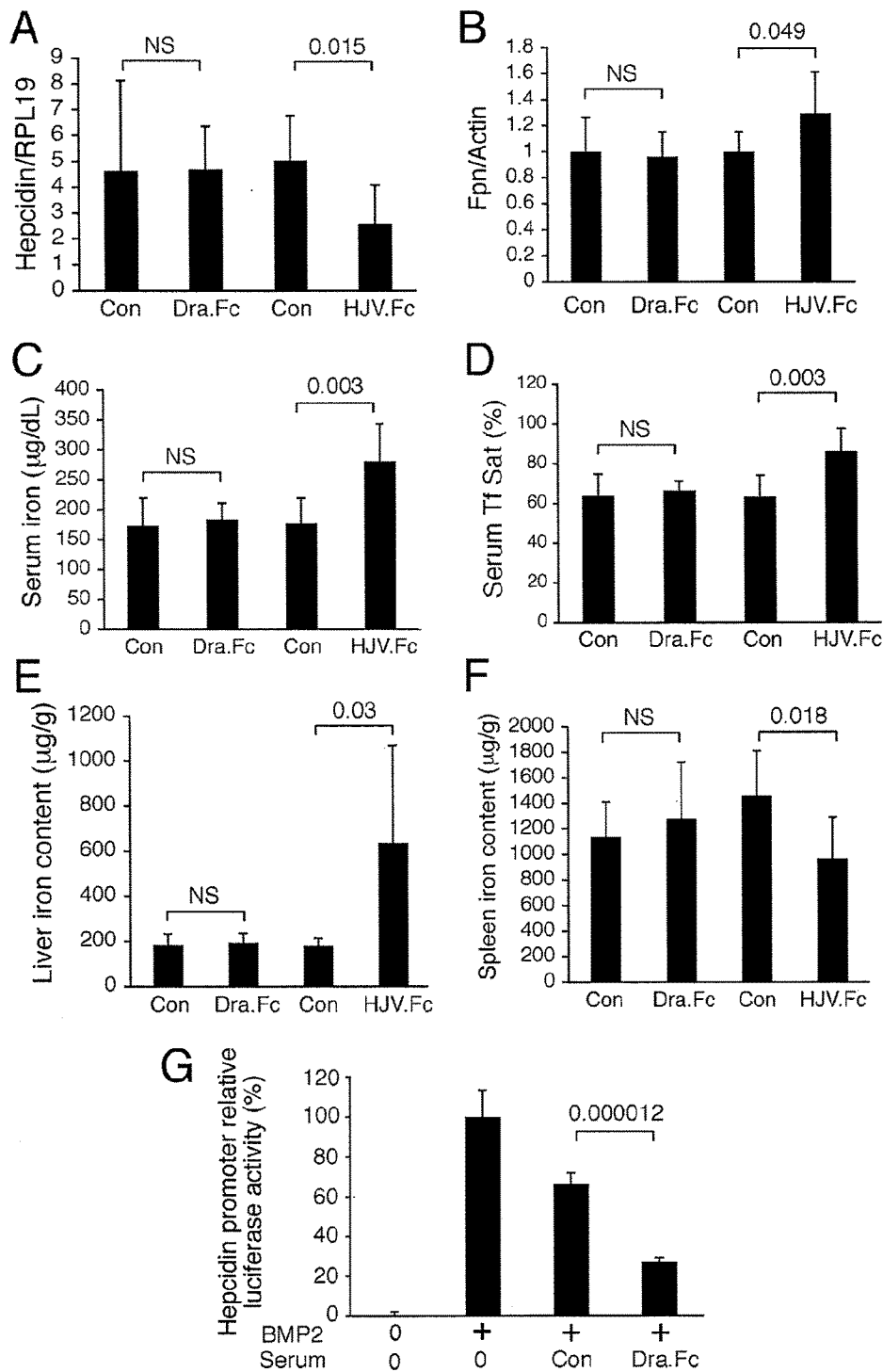
FIGS. 2A-2G show evidence that DRAGON.Fc administration in mice does not affect hepcidin expression or iron metabolism.

DRAGON.Fc Administration in Mice does not Affect Hepcidin Expression or Iron Metabolism FIG. 2. Eight week-old male 129S6/SvEvTac mice received an intraperitoneal injection of purified soluble DRAGON.Fc (Dra.Fc) at 5 (n=3) or 10 mg/kg (n=4) or an equal volume of isotonic saline (Con, n=7) three times weekly for three weeks. As a positive control, another group of mice received an intraperitoneal injection of an equivalent amount of HJV.Fc at 5 (n=3) or 7 mg/kg (n=4) or an equal volume of isotonic saline (Con, n=7) three times weekly for three weeks. Results for both DRAGON.Fc and HJV.Fc doses were similar and were therefore combined into one group. (A) Total liver RNA was isolated and analyzed by quantitative real-time RT-PCR for hepcidin mRNA relative to RPL19 mRNA as an internal control. (B) Spleen membrane preparations were analyzed for ferroportin (FPN) expression by Western blot. Blots were stripped and probed with anti-p-actin antibody as a loading control. Chemiluminescence was quantitated by IPLab Spectrum software for ferroportin relative to p-actin expression. (C and D) Measurement of serum iron (C) and transferring saturation (D). (E and F) quantitation of liver (E) and spleen (F) tissue iron content. (G) Hep3B cells were transfected with a hepcidin promoter luciferase reporter and pRL-TK as in FIG. 1. Forty eight hours after transfection, cells were incubated in the absence or presence of 1 ng/mL BMP-2, either alone or in combination with 20% pooled serum from mock treated control mice (Con, n=4) or from DRAGON.Fc treated mice (Dra.Fc, n=4) for sixteen hours. Relative luciferase activity was calculated as in FIG. 1. Results are reported as the mean+I−s.d. Exact P values are shown.

Example 13

Figure 3:
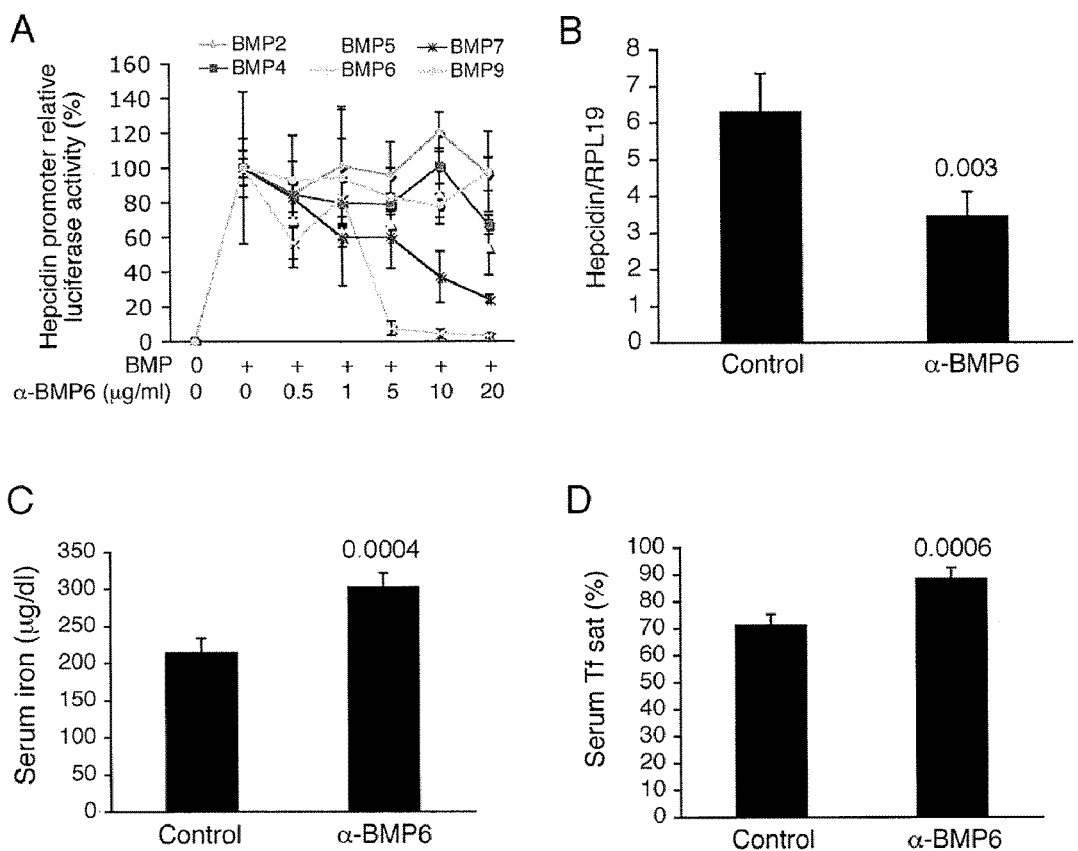
FIGS. 3A-3D show s evidence that pecific neutralizing BMP-6 antibody inhibits hepatic hepcidin expression and increases serum iron and transferrin saturation in vivo.

Specific Neutralizing BMP-6 Antibody Inhibits Hepatic Hepcidin Expression And Increases Serum Iron and Transferrin Saturation In vivo FIG. 3. (A) Hep3B cells were transfected with a hepcidin promoter luciferase reporter and control pRL-TK as in FIG. 1. Forty-eight hours after transfection, cells were incubated in the absence or presence of BMP-2, BMP-4, BMP-5, BMP-6, BMP-7, or BMP-9 ligands, either alone or in combination with 0.2 to 25 μg/mL neutralizing BMP-6 antibody as shown (n=2 per group). Relative luciferase activity was calculated as in FIG. 1. (B-D) Eight week-old male 129S6/SvEvTac mice received an intraperitoneal injection of neutralizing BMP-6 antibody at 10 mg/kg (a-BMP-6, n=4) or an equal volume of isotonic saline (Control, n=4) daily for three days. (B) Total liver RNA was isolated and analyzed by quantitative real-time RT-PCR for hepcidin mRNA relative to RPL19 mRNA as an internal control. (C and D) Measurement of serum iron (C) and transferrin saturation (D). Results are expressed as the mean+I— s.d. Exact P values are shown.

Example 14

Bmp6 Null Mice Exhibit Reduced Hepatic Hepcidin Expression, Increased Spleen Ferroportin Expression, Increased Serum Iron and Transferrin Saturation, Increased Liver Iron Content and Reduced Spleen Iron Content FIG. 4. Eight-week-old male Bmp6 null mice (n=5) and strain matched wildtype control mice (WT, n=5) were analyzed for (A) hepcidin mRNA expression relative to RPL19 mRNA expression by quantitative real-time RT-PCR, (B and C) ferroportin expression relative to p-actin expression by Western blot (C) followed by quantitation using IPLab Spectrum software (B), (D) serum iron, (E) serum transferrin saturation, (F) liver iron content, (G) and spleen iron content as described in FIG. 2. (H) Perls Prussian blue staining of tissue iron in wildtype (WT) and a Bmp6 null mouse livers. Original magnification×10. Results are expressed as mean+/−s.d. Exact P values are shown.

Example 15

Figure 5:
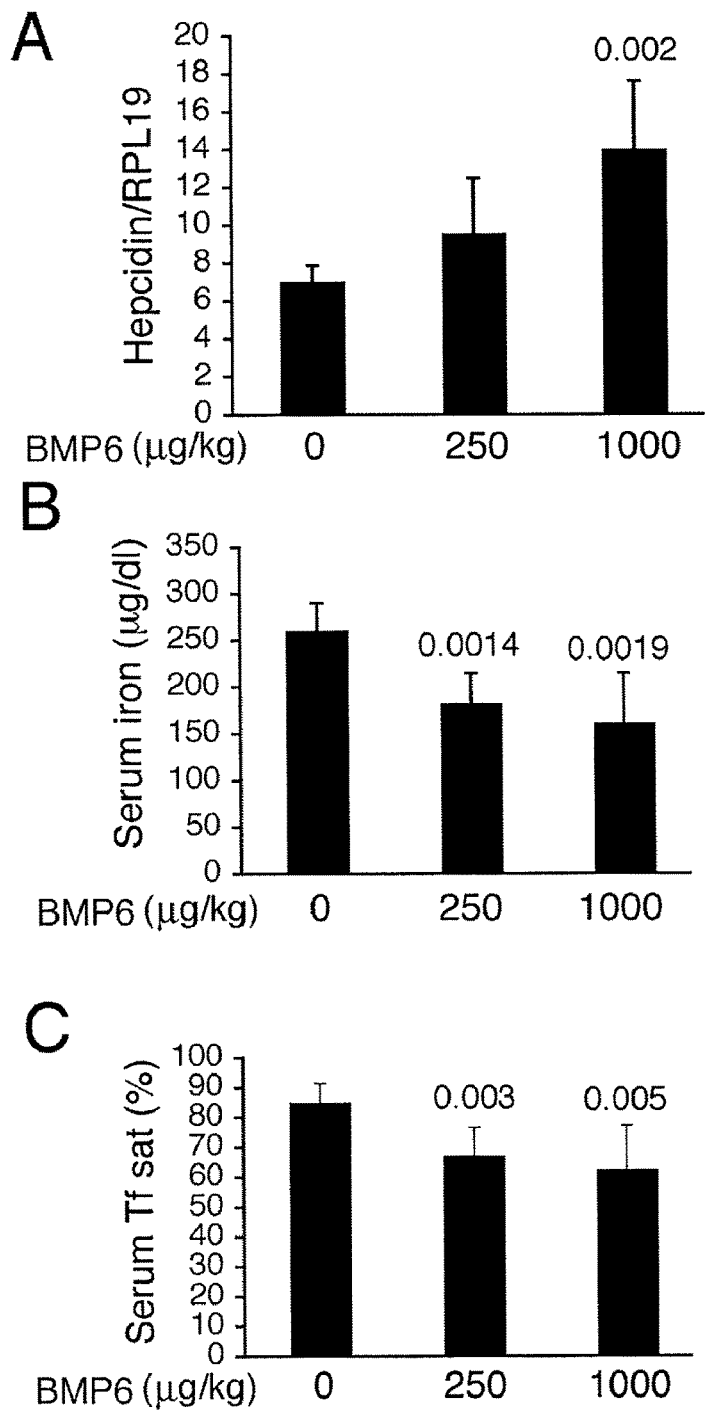
FIGS. 5A-5C show evidence that BMP-6 administration in mice increases hepcidin mRNA expression and reduces serum iron.
Figure 6:
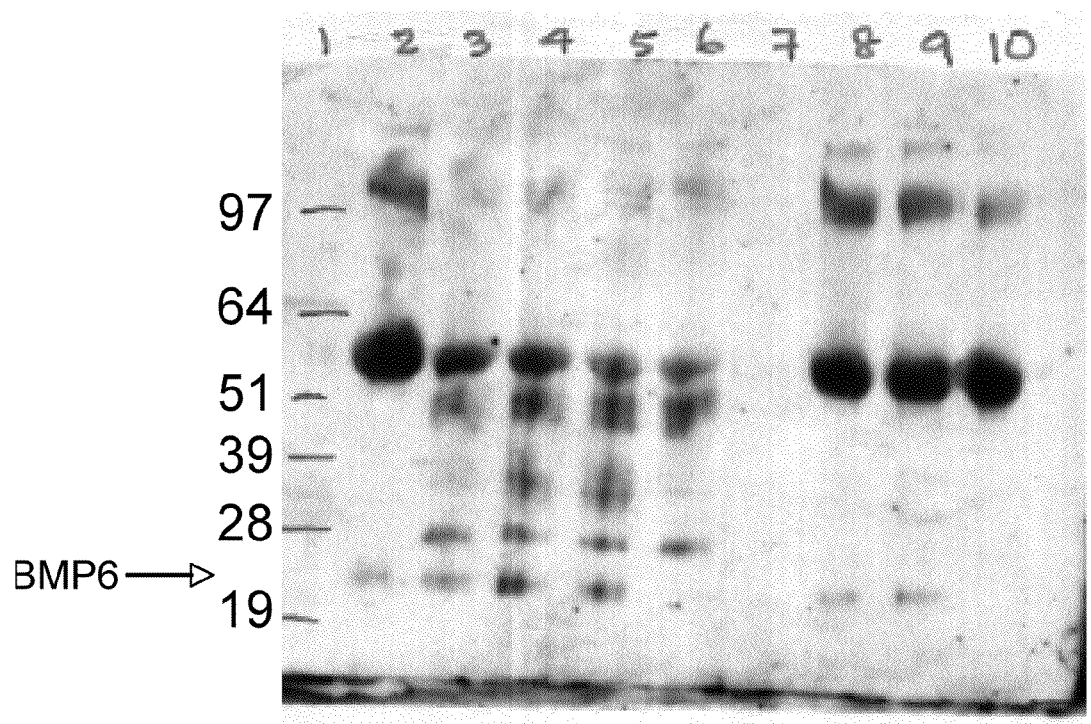
FIG. 6 is a Western blot for BMP-6.
Figure 7:
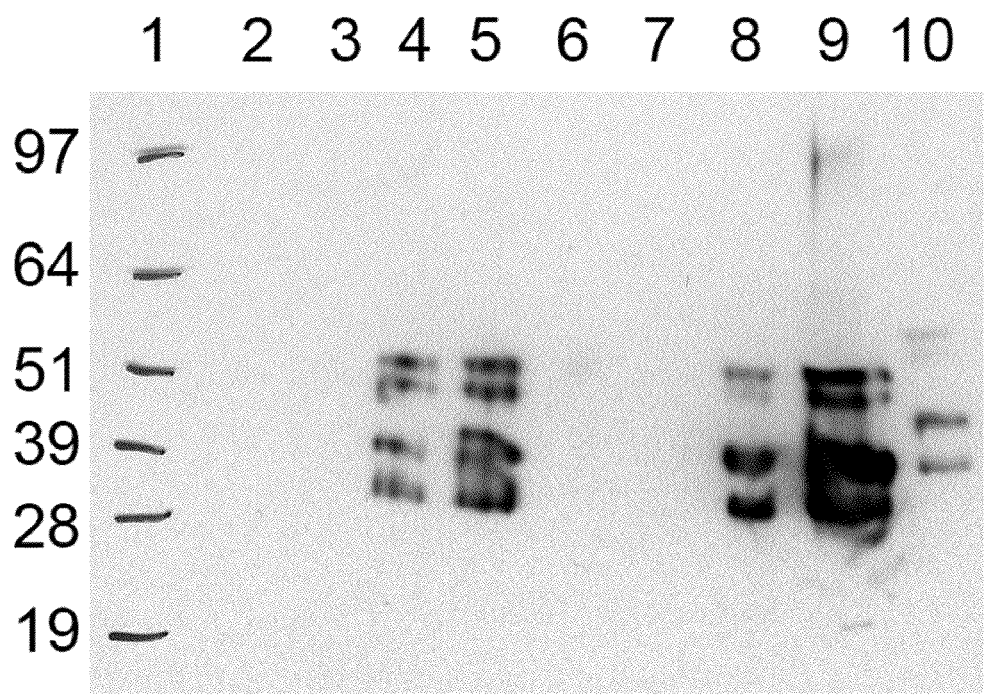
FIG. 7 is a Western blot for HJV.

BMP-6 Administration in Mice Increases Hepcidin mRNA Expression and Reduces Serum Iron FIG. 5. Eight-week-old male 12956/SvEvTac mice received an intraperitoneal injection of BMP-6 at 250 μg/kg (n=6) or 1000 μg/kg (n=7) or an equal volume of vehicle alone (n=6). Six hours after injection, blood and livers were harvested. (A) Total liver RNA was isolated and analyzed by quantitative real-time RT PCR for hepcidin mRNA relative to RPL19 mRNA as an internal control. (B and C) Measurement of serum iron (B) and transferrin saturation (C). Results are reported as the mean+/−s.d. Exact P values are shown.

Example 16

Preparation of *Brucella abortus* for Intraperitoneal Injection Used In Mouse Models of Anemia

*Brucella abortus* (BA) is used to induce an inflammatory anemia when injected intraperitoneally (IP) into mice. Resultant anemia usually established within 7 days, characterized by 2-3 g/dL drop in hemoglobin levels. The anemia typically lasts 28 days post injection. After 28 days the mice start to recover and see hemoglobin levels start to rise. This protocol describes how to 1) wash and separate BA particles from phenolized buffer and 2) prepare BA for IP delivery of $5\times10^8$ particles/mouse in a volume of 200 μL for 10 mice.

A $5\times10^9$ stock is washed and prepared in the following manner. First, 60 mL bottles are removed from refrigerator and mix completely. 500 ml of BA is then transferred into 500 mL centrifuge bottle. These are then centrifuges at 10,000 rpm for 15 mins using an Ultracentrifuge. The supernatant is removed and resuspend in 100 mL PBS. Suspension is now $5\times10^9$ particles/mL. Aliquot and freeze at −80° C., typically at 1 mL aliquots.

$5\times10^8$ particles for injection are prepared in the following manner (example for 10 mice). Starting concentration needs to be $2.5\times10^9$ particles/mL since 200 μL/mouse will be injected. Dilute stock 2-fold using PBS. For example, 10 mice×0.200 μL=2 mL+20% overage=2.2 mL of $2.5\times10^9$ particles/mL needed. 1.1 mL BA stock+1.1 mL PBS.

Materials

BA: *Brucella abortus* Ring Test Antigen (strain 1119-3) in 60 mL bottles can be purchased from U.S. Department of Agriculture, Animal and Plant Health Inspection Service, National Veterinary Services Laboratories, Ames, Iowa. Brucellosis ring test antigen contains a suspension of killed, stained *B. abortus* strain 1119-3 cells in phenolized buffer. The concentration of each 60 mL bottle is approximately $10^9$particles/mL. Antigen stored at 4° C.

Diluent: DPBS (Gibco) used washing agent, carrier and control.

Results

Antibodies that specifically bind to BMP-6 are administered to mice subject to the intraperitoneal injection of *Brucella abortus*. Antibodies that diminish or abolish symptoms of inflammatory anemia in mice from intraperitoneal injection of *Brucella abortus* are appropriate to be used to treat anemia in mammals.

Example 17

Binding on Multiple Sites on BMP-6 Inhibits Hepatic Hepcidin Expression and Increases Serum Iron and Transferrin Saturation A pulldown assay was performed to ascertain whether HJV and the BMP-6 antibody used in Example 13, above, bind BMP-6 at the same site.

hBMP6 (1 μg)+/−hHJV.H is (7.1 μg for 5× or 35.5 μg for 25× molar ratio to mAb) was incubated in 500 μl saline solution overnight at 4° C. Then 2.5 μg mAb (mAb507, R&D Systems) was added for 1 hr, before pull-down with Protein A beads. Samples were then run on SDS-PAGE gel 4-12%, and transferred to PVDF membrane. The Western blot analysis shown in FIG. 6, was performed with a rabbit polyclonal anti-BMP6 antibody as primary antibody, and goat anti-rabbit IgG-HRP as secondary Ab. The blot was developed with ECL reagent, exposed for 3 minutes. The BMP6 protein band is indicated by the arrow and is present only in samples containing BMP6 (Lanes 2, 3, 4, 5, 8 and 9) but not present in samples without BMP6 (Lanes 6, 7 and 10).

Lanes:

1. See Blue Plus 2 Prestained MW ladder
2. Pre-IP aliquot of hBMP6+mAb mixture
3. IP of hBMP6+mAb
4. IP of hBMP6+mAb+5×hHJV.H is
5. IP of hBMP6+mAb+25×hHJV.H is
6. IP of mAb only
7. Blank
8. Pre-IP aliquot of hBMP6+mAb+5×hHJV.H is
9. Pre-IP aliquot of hBMP6+mAb+25×hHJV.H is
10. Pre-IP aliquot of mAb Results:

Anti-BMP6 mAb (R&D Systems) pulled down hBMP6, as shown in FIG. 6, lane 3. Addition of molar excess hHJV.H is did not inhibit pull down as shown in FIG. 6, lanes 4 and 5. Based on this we recognized that hHJV.H is and anti-BMP6 may be binding to different sites on hBMP6. Next the blot was checked for the presence of hHJV.his to see if it was also pulled down.

FIG. 7 shows the same blot as shown in FIG. 6, after stripping, and being reprobed with mAb 24C8-C10 (specific for HJV) to visualize hHJV.His. As shown in FIG. 7, anti-BMP6 mAb (R&D Systems) pulled down hHJV.H is protein in the presence of hBMP6 (lanes 4 and 5). Thus, we concluded that hHJV.his and anti-BMP6 bind to non-overlapping sites on hBMP6, a non-obvious result.

Example 18 hBMP-6 Peptide for Use in Raising Antibodies to BMP-6

Antibodies have been made against the hBMP6 peptide TQSQDVARVSSASDY.

A Western blot analysis assay was performed to demonstrate that it is possible to generate antibodies to a specific peptide domain in mature hBMP6 defined as TQSQDVARVSSASDY (SEQ ID NO:3).

Figure 8:
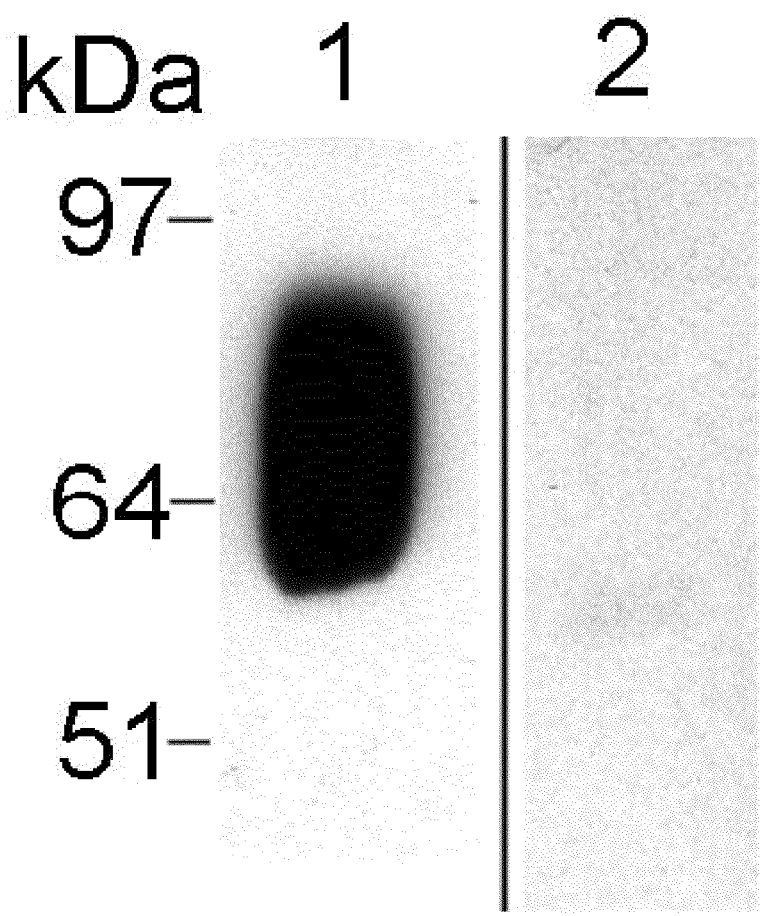
FIG. 8 is a Western blot of hBMP-6.

Goat polyclonal anti-hBMP6 antibodies (R and D Systems AF507) specifically detect bovine serum albumin (BSA) conjugated to hBMP6 peptide by a Cysteine residue (BSA-C-TQSQDVARVSSASDY (SEQ ID NO:4)) (FIG. 8, lane 1).

Competition with 500× molar excess of the unconjugated hBMP6 peptide eliminated the binding of the polyclonal antibody to BSA-C-TQSQDVARVSSASDY (SEQ ID NO:4) (FIG. 8, lane 2).

This indicates it is possible to generate antibodies to a specific peptide domain in mature hBMP6 defined as TQSQDVARVSSASDY (SEQ ID NO:3).

References

Each one of the following references is incorporated herein by reference as if set forth herein in its entirety:
1. Roetto, A., et al. 2003. Nat. Genet. 33:21-22.
2. Papanikolaou, G., et a/0.2004. Nat. Genet. 36:77-82.
3. Babitt, J. L., et al. 2006. Nat. Genet. 38:531-539.
4. Babitt, J. L., et al. 2007. J Clin Invest. 117:1933-1939.
5. Shi, Y., and Massague, J. 2003. Cell. 113, 685-700.
6. Wang, R. H., et al. 2005. Cell Metab. 2:399-409.
7. Pigeon, C., et al. 2001. J. Biol. Chem. 276:7811-7819.
8. Nemeth, E., et al. 2004. Science. 306:2090-2093.
9. Nicolas, G., et al. 2002. J. Clin. Invest. 110:1037-1044
10. Nemeth, E., et al. 2004. J. Clin. Invest. 113: 1271-1276.
11. Pietrangelo, A. 2006. 1763:700-710.
12. Nemeth, E., et al. 2003. Blood. 101:246 1-2463.
13. Weiss, G. and Goodnough, L. T. 2005. N. Engl. J. Med. 352:1011-1023.
14. Andrews N C. 2008. Blood. 1122 19-30.
15. Huang, F. W., et al. J. Clin. Invest. 115:2187-2191.
16. Niederkofler, V., Salie, R., Arber, S. 2005. J Clin Invest. 115:2180-6.
17. Truksa, J., et al. 2006. Proc. Natl. Acad. Sci. USA. 103:10289-10293.
18. Verga Falzacappa, M. V., et al. 2008. J Mol. Med. 86:531-40.
19. Yu, P. B., et al. 2008. Nat Chem. Biol. 4:33-41.
20. Samad, T. A., et al. 2004. J. Neurosci. 24:2027-2036.
21. Babitt, J. L., et al. 2005. J. Biol. Chem. 280:29820-29827.
22. Samad, T. A., et al. 2005. J. Biol. Chem. 280:14122-14129.
23. Balemans, W., Van Hul, W. 2002. Dev Biol. 250:231-50.
24. Solloway M J, et al. 1998. Dev Genet. 22:321-39.
25. Xia Y, et al. 2008. Blood. 1115 195-204.
26. Kautz, L., et al. 2008. Blood. 112:1503-9.
27. Simic, P., et a/0.2006. J Biol. Chem. 281:25509-21.
28. Xia, Y., et al. 2007. J Biol. Chem. 282:18129-40.
29. Knutson, M. D., et al. 2005. Proc Natl Acad Sci USA 0.102:1324-8.
30. Andriopoulos, B. et al 2009. Nat. Genet. 41(4):482-7.

Each one of the following patent references is incorporated herein by reference in its entirety: PCT application No. PCT1/US08/059,753, filed on Apr. 9, 2008; U.S. patent application Ser. No. 11/884,509, filed on Aug. 16, 2007; U.S. patent application Ser. No. 11/195,205, filed on Aug. 2, 2005; and U.S. patent application Ser. No. 10/419,296, filed on Apr. 17, 2003.

All publications and patent applications cited in this specification are herein incorporated by reference as if each individual publication or patent application are specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for increasing serum iron levels in a subject, said method comprising administering to said subject an effective amount of a pharmaceutical composition sufficient for modulating BMP-6 signaling at a level sufficient to increase serum iron levels in the subject, wherein the pharmaceutical composition is a monoclonal antibody that specifically binds mature BMP-6 protein or fragments thereof, and wherein the antibody competitively inhibits BMP-6 binding to soluble human hemojuvelin protein.

2. The method of claim 1, wherein administering the composition reduces BMP-6 signaling.

3. The method of claim 1, wherein the mature BMP-6 comprises the amino acid sequence of SEQ ID NO:2.

4. The method of claim 1, wherein the composition binds BMP-6 within residues TQSQDVARVSSASDY (SEQ ID NO:3).

5. The method of claim 1, wherein the soluble human hemojuvelin protein is HJV.Fc or HJV.His.

6. The method of claim 1, wherein administering the composition reduces hemojuvelin-mediated induction of hepcidin expression.

7. The method of claim 6, wherein the composition is administered in an amount sufficient to inhibit an interaction between hemojuvelin and BMP-6.

8. The method of claim 7, wherein the composition preferably inhibits human BMP-6 over BMP-2, BMP-4, BMP-5, BMP-7 or BMP-9.

9. The method of claim 8, wherein the composition binds BMP-6 with at least 5-fold greater affinity that BMP-7.

10. The method of claim 1, wherein the administration of the composition results in increased serum transferrin saturation in the subject.

11. A method of treating a disorder of serum iron deficiency in a subject in need thereof comprising administering to said subject the antibody of claim 1.

12. The method of claim 11, wherein the disorder of serum iron deficiency is anemia.

* * * * *

UNITED STATES PATENT AND TRADEMARK OFFICE
CERTIFICATE OF CORRECTION

PATENT NO.       : 8,318,167 B2
APPLICATION NO.  : 12/618319
DATED            : November 27, 2012
INVENTOR(S)      : Herb Lin et al.

Page 1 of 1

It is certified that error appears in the above-identified patent and that said Letters Patent is hereby corrected as shown below:

In the Claims:

Column 39, Line 11, Claim 9, "that" should read --than--

Signed and Sealed this
Twentieth Day of August, 2013

Teresa Stanek Rea
*Acting Director of the United States Patent and Trademark Office*

SEQUENCE LISTING

```
<160> NUMBER OF SEQ ID NOS: 4

<210> SEQ ID NO 1
<211> LENGTH: 428
<212> TYPE: PRT
<213> ORGANISM: Homo sapiens
<220> FEATURE:
<221> NAME/KEY: PROPEP
<222> LOCATION: (1)..(428)
<223> OTHER INFORMATION: Human pro-BMP-6

<400> SEQUENCE: 1

Asp Cys Ser Arg Gln Gly Pro Gln Arg Pro Arg Ser Gly Leu Ala Pro
1               5                   10                  15

Pro Gln Pro Pro Ala Leu Arg Gln Gln Glu Glu Gln Gln Gln Gln Gln
            20                  25                  30

Gln Leu Pro Arg Gly Glu Pro Pro Gly Arg Leu Lys Ser Ala Pro
        35                  40                  45

Leu Phe Met Leu Asp Leu Tyr Asn Ala Leu Ser Ala Asp Asn Asp Glu
    50                  55                  60

Asp Gly Ala Ser Glu Gly Glu Arg Gln Gln Ser Trp Pro His Glu Ala
65                  70                  75                  80

Ala Ser Ser Ser Gln Arg Arg Gln Pro Pro Pro Gly Ala Ala His Pro
                85                  90                  95

Leu Asn Arg Lys Ser Leu Leu Ala Pro Gly Ser Gly Ser Gly Gly Ala
```

```
                100                 105                 110
Ser Pro Leu Thr Ser Ala Gln Asp Ser Ala Phe Leu Asn Asp Ala Asp
            115                 120                 125

Met Val Met Ser Phe Val Asn Leu Val Glu Tyr Asp Lys Glu Phe Ser
130                 135                 140

Pro Arg Gln Arg His His Lys Glu Phe Lys Phe Asn Leu Ser Gln Ile
145                 150                 155                 160

Pro Glu Gly Glu Val Val Thr Ala Ala Glu Phe Arg Ile Tyr Lys Asp
                165                 170                 175

Cys Val Met Gly Ser Phe Lys Asn Gln Thr Phe Leu Ile Ser Ile Tyr
            180                 185                 190

Gln Val Leu Gln Glu His Gln His Arg Asp Ser Asp Leu Phe Leu Leu
        195                 200                 205

Asp Thr Arg Val Val Trp Ala Ser Glu Glu Gly Trp Leu Glu Phe Asp
    210                 215                 220

Ile Thr Ala Thr Ser Asn Leu Trp Val Val Thr Pro Gln His Asn Met
225                 230                 235                 240

Gly Leu Gln Leu Ser Val Val Thr Arg Asp Gly Val His Val His Pro
                245                 250                 255

Arg Ala Ala Gly Leu Val Gly Arg Asp Gly Pro Tyr Asp Lys Gln Pro
            260                 265                 270

Phe Met Val Ala Phe Phe Lys Val Ser Glu Val His Val Arg Thr Thr
        275                 280                 285

Arg Ser Ala Ser Ser Arg Arg Arg Gln Gln Ser Arg Asn Arg Ser Thr
    290                 295                 300

Gln Ser Gln Asp Val Ala Arg Val Ser Ser Ala Ser Asp Tyr Asn Ser
305                 310                 315                 320

Ser Glu Leu Lys Thr Ala Cys Arg Lys His Glu Leu Tyr Val Ser Phe
                325                 330                 335

Gln Asp Leu Gly Trp Gln Asp Trp Ile Ile Ala Pro Lys Gly Tyr Ala
            340                 345                 350

Ala Asn Tyr Cys Asp Gly Glu Cys Ser Phe Pro Leu Asn Ala His Met
        355                 360                 365

Asn Ala Thr Asn His Ala Ile Val Gln Thr Leu Val His Leu Met Asn
    370                 375                 380

Pro Glu Tyr Val Pro Lys Pro Cys Cys Ala Pro Thr Lys Leu Asn Ala
385                 390                 395                 400

Ile Ser Val Leu Tyr Phe Asp Asp Asn Ser Asn Val Ile Leu Lys Lys
                405                 410                 415

Tyr Arg Asn Met Val Val Arg Ala Cys Gly Cys His
            420                 425
```

<210> SEQ ID NO 2
<211> LENGTH: 132
<212> TYPE: PRT
<213> ORGANISM: Homo sapiens
<220> FEATURE:
<221> NAME/KEY: mat_peptide
<222> LOCATION: (1)..(132)
<223> OTHER INFORMATION: Human BMP-6 (hBMP-6)

```
<400> SEQUENCE: 2

Gln Gln Ser Arg Asn Arg Ser Thr Gln Ser Gln Asp Val Ala Arg Val
1               5                   10                  15

Ser Ser Ala Ser Asp Tyr Asn Ser Ser Glu Leu Lys Thr Ala Cys Arg
            20                  25                  30

Lys His Glu Leu Tyr Val Ser Phe Gln Asp Leu Gly Trp Gln Asp Trp
        35                  40                  45

Ile Ile Ala Pro Lys Gly Tyr Ala Ala Asn Tyr Cys Asp Gly Glu Cys
    50                  55                  60

Ser Phe Pro Leu Asn Ala His Met Asn Ala Thr Asn His Ala Ile Val
65                  70                  75                  80

Gln Thr Leu Val His Leu Met Asn Pro Glu Tyr Val Pro Lys Pro Cys
                85                  90                  95

Cys Ala Pro Thr Lys Leu Asn Ala Ile Ser Val Leu Tyr Phe Asp Asp
            100                 105                 110

Asn Ser Asn Val Ile Leu Lys Lys Tyr Arg Asn Met Val Val Arg Ala
            115                 120                 125

Cys Gly Cys His
    130

<210> SEQ ID NO 3
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: h-BMP6 peptide fragment

<400> SEQUENCE: 3

Thr Gln Ser Gln Asp Val Ala Arg Val Ser Ser Ala Ser Asp Tyr
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: bovine serum albumin (BSA) conjugated via
      Cysteine
<220> FEATURE:
<221> NAME/KEY: PEPTIDE
<222> LOCATION: (2)..(16)
<223> OTHER INFORMATION: h-BMP6 peptide fragment

<400> SEQUENCE: 4

Cys Thr Gln Ser Gln Asp Val Ala Arg Val Ser Ser Ala Ser Asp Tyr
1               5                   10                  15
```